US010533970B2

(12) United States Patent
Dusseault et al.

(10) Patent No.: US 10,533,970 B2
(45) Date of Patent: Jan. 14, 2020

(54) SYSTEM AND METHOD FOR DETECTING IRREGULARITIES IN REBAR IN REINFORCED CONCRETE

(71) Applicants: Maurice Bernard Dusseault, Waterloo (CA); Seyedbijan Mahbaz, Waterloo (CA)

(72) Inventors: Maurice Bernard Dusseault, Waterloo (CA); Seyedbijan Mahbaz, Waterloo (CA)

(*) Notice: Subject to any disclaimer, the term of this patent is extended or adjusted under 35 U.S.C. 154(b) by 217 days.

(21) Appl. No.: 15/620,883

(22) Filed: Jun. 13, 2017

(65) Prior Publication Data
US 2018/0059060 A1 Mar. 1, 2018

Related U.S. Application Data

(60) Provisional application No. 62/382,460, filed on Sep. 1, 2016.

(51) Int. Cl.
*G01N 27/82* (2006.01)
*G01N 33/38* (2006.01)

(52) U.S. Cl.
CPC .......... *G01N 27/82* (2013.01); *G01N 33/383* (2013.01)

(58) Field of Classification Search
CPC .............................. G01N 27/82; G01N 33/383
See application file for complete search history.

(56) References Cited

U.S. PATENT DOCUMENTS

| 5,570,017 | A | * | 10/1996 | Blum | G01N 27/82 324/232 |
| 5,650,725 | A | * | 7/1997 | Powell | G01V 3/08 324/326 |
| 7,095,223 | B2 | | 8/2006 | Yoo | |
| 2002/0154029 | A1 | * | 10/2002 | Watters | G01D 5/48 340/870.07 |
| 2003/0146749 | A1 | | 8/2003 | Srinivasan et al. | |

(Continued)

FOREIGN PATENT DOCUMENTS

| CN | 106198368 A | 12/2016 |
| WO | 96/28727 | 9/1996 |

(Continued)

OTHER PUBLICATIONS

Machine Generated English Language Translation of CN 106198368, published on Dec. 7, 2016.

*Primary Examiner* — Akm Zakaria

(57) ABSTRACT

A system for determining whether a magnetic field associated with an elongate rebar element in a concrete body of a reinforced structural element assembly includes one or more anomalies. The system includes a data-gathering unit having a frame assembly movable relative to the reinforced structural element assembly, and a sensor assembly mounted to the frame assembly. The sensor assembly includes one or more magnetic sensors for sensing at least part of the magnetic field as the sensor assembly is moved relative to the concrete body, to generate magnetic field data defining magnetic flux density of the magnetic field of the rebar element. The system also includes a tracking assembly for generating location data to locate the magnetic field data relative to the concrete body, and a processor for analyzing the magnetic field data and the location data to generate anomaly data describing the anomaly.

1 Claim, 21 Drawing Sheets

(56) References Cited

U.S. PATENT DOCUMENTS

| | | | |
|---|---|---|---|
| 2010/0102809 A1* | 4/2010 | May | G01R 33/022 |
| | | | 324/244 |
| 2015/0025805 A1 | 1/2015 | Hanak et al. | |
| 2016/0025680 A1* | 1/2016 | Schein, Jr. | G01N 27/82 |
| | | | 324/228 |
| 2016/0363549 A1* | 12/2016 | Mazzeo | G01N 17/04 |

FOREIGN PATENT DOCUMENTS

| | | |
|---|---|---|
| WO | 2006/103483 A2 | 10/2006 |
| WO | 2015/120550 A1 | 8/2015 |

* cited by examiner

SYSTEM AND METHOD FOR DETECTING IRREGULARITIES IN REBAR IN REINFORCED CONCRETE

CROSS-REFERENCE TO RELATED APPLICATION

This application claims the benefit of U.S. Provisional Patent Application No. 62/382,460, filed on Sep. 1, 2016, the entirety of which is hereby incorporated herein by reference.

FIELD OF THE INVENTION

The present invention is a system and a method for determining whether a magnetic field associated with a rebar element in a reinforced structural element assembly includes one or more anomalies.

BACKGROUND OF THE INVENTION

Reinforced concrete is widely used in many structures. For various reasons, reinforced concrete may deteriorate over time. For example, in locations where the weather is often wet and cold, salt is used to de-ice roads and parking lots. The salt causes deterioration of the concrete and, ultimately, corrosion of rebar in the reinforced concrete, potentially affecting the load-bearing ability of the reinforced concrete. Corrosion of the rebar is the result of weathering. As is well known in the art, ambient temperature fluctuations and the presence of salt tend to increase the rate of corrosion.

A typical reinforced concrete beam 10 is illustrated in FIG. 1. The beam 10 includes a body 12 in which rebar 14 is positioned. As is well known in the art, the rebar 14 is made of steel, and the body 12 is made of concrete that generally or at least substantially encases the rebar 14. Although only one rebar element 14 is illustrated in FIG. 1, it will be understood that the reinforced concrete beam 10 may alternatively include a number of elongate rebar elements, positioned substantially parallel to each other. As can be seen in FIG. 1, the rebar 14 is generally not directly observable, because it is encased in the body 12. At its ends, the rebar 14 may be directly observable, depending on the position of the reinforced concrete beam 10 in the structure in which it is included. In FIG. 1, a corroded area 16 is indicated by dashed lines, for clarity of illustration. Corrosion of the rebar 14 may occur at any point or points along the length of the rebar, and therefore the rebar may have significant corrosion that is not directly observable, if the body is left intact. (As will be described, the balance of the drawings illustrate the present invention.)

Corrosion of the rebar undermines the load-bearing capacity of the reinforced concrete in which the rebar is located. Therefore, detection of such corrosion can be critical. As is well known in the art, detecting corrosion of the rebar in reinforced concrete in an existing structure in most cases would not be possible with visual methods, or without destruction of at least part of the reinforced concrete. However, visual detection or destructive testing of the reinforced concrete in an existing structure are also usually not feasible.

In the prior art, corrosion may be detected when the concrete at a readily accessible portion of the structure has deteriorated to the extent that the corroded rebar is exposed. However, at that point, the poor condition of the reinforced concrete may require emergency action to repair the structure. Also, repairs are of necessity limited to damaged areas that are exposed, and such repairs would not address other damage that may have occurred to the rebar elsewhere in the reinforced concrete.

SUMMARY OF THE INVENTION

For the foregoing reasons, there is a need for a system and method for detecting irregularities in rebar in reinforced concrete that overcomes or mitigates one or more of the disadvantages or defects of the prior art. Such disadvantages or defects are not necessarily included in those described above.

In general terms, the invention herein provides a non-destructive method and system for detecting irregularities in the rebar in reinforced concrete in situ. In its broad aspect, the invention provides a system for determining whether a magnetic field associated with an elongate rebar element at least partially positioned in a concrete body of a reinforced structural element assembly includes one or more anomalies. The system includes a data-gathering unit having a frame assembly, movable relative to the reinforced structural element assembly in a preselected direction along a preselected path at a preselected velocity, and a sensor assembly mounted to the frame assembly. The sensor assembly includes one or more magnetic sensors for sensing at least part of the magnetic field as the sensor assembly is moved relative to the concrete body, to generate magnetic field data defining magnetic flux density of the magnetic field of the rebar element. The system also includes a tracking assembly for generating location data to locate the magnetic field data relative to the concrete body, and a processor for analyzing the magnetic field data for identifying the one or more anomalies, for analyzing the location data to locate the one or more anomalies relative to the concrete body, and for generating anomaly data describing the one or more anomalies.

In another of its aspects, the invention provides a method for determining whether a magnetic field associated with a rebar element at least partially positioned in a concrete body of a reinforced structural element assembly includes one or more anomalies. The method includes providing one or more magnetic sensors, for sensing at least part of the magnetic field, and moving a data-gathering unit that includes the magnetic sensor(s) relative to the reinforced structural element assembly, to generate magnetic field data defining magnetic flux density of the magnetic field of the rebar element. With a tracking assembly, location data is generated, to locate the magnetic field data relative to the concrete body. The magnetic field data and the location data are transmitted to a processor. With the processor, the data is analyzed to identify the anomaly, and for analyzing the location data to locate the one or more anomalies relative to the concrete body, to provide the anomaly data.

BRIEF DESCRIPTION OF THE DRAWINGS

The invention will be better understood with reference to the attached drawings, in which.

DETAILED DESCRIPTION

Figure 4:
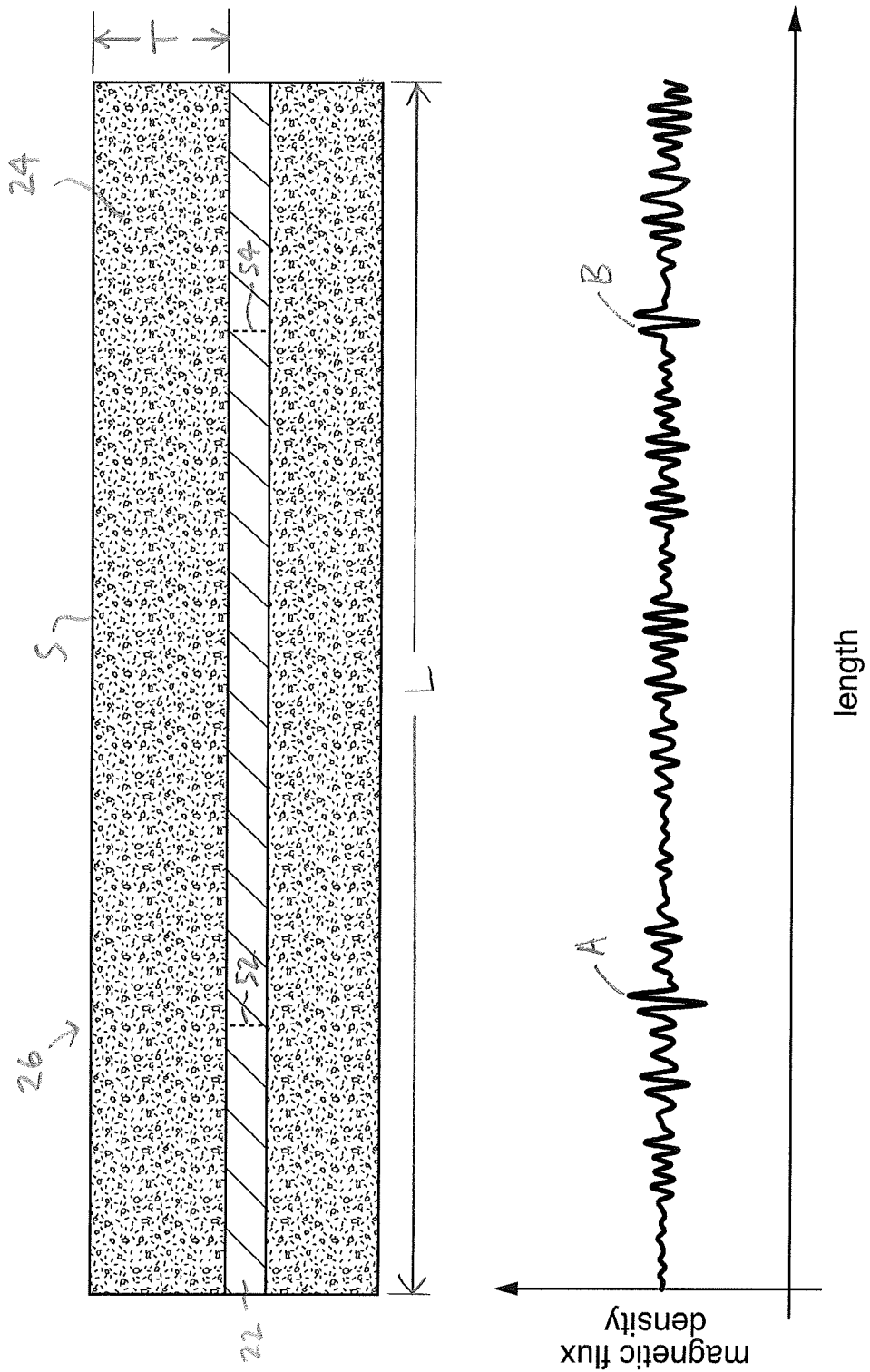
FIG. 4 is a composite view in which a cross-section of the reinforced concrete assembly is positioned adjacent to a graph of the magnetic flux density of the magnetic field associated with a rebar element of the reinforced concrete assembly.
Figure 5:
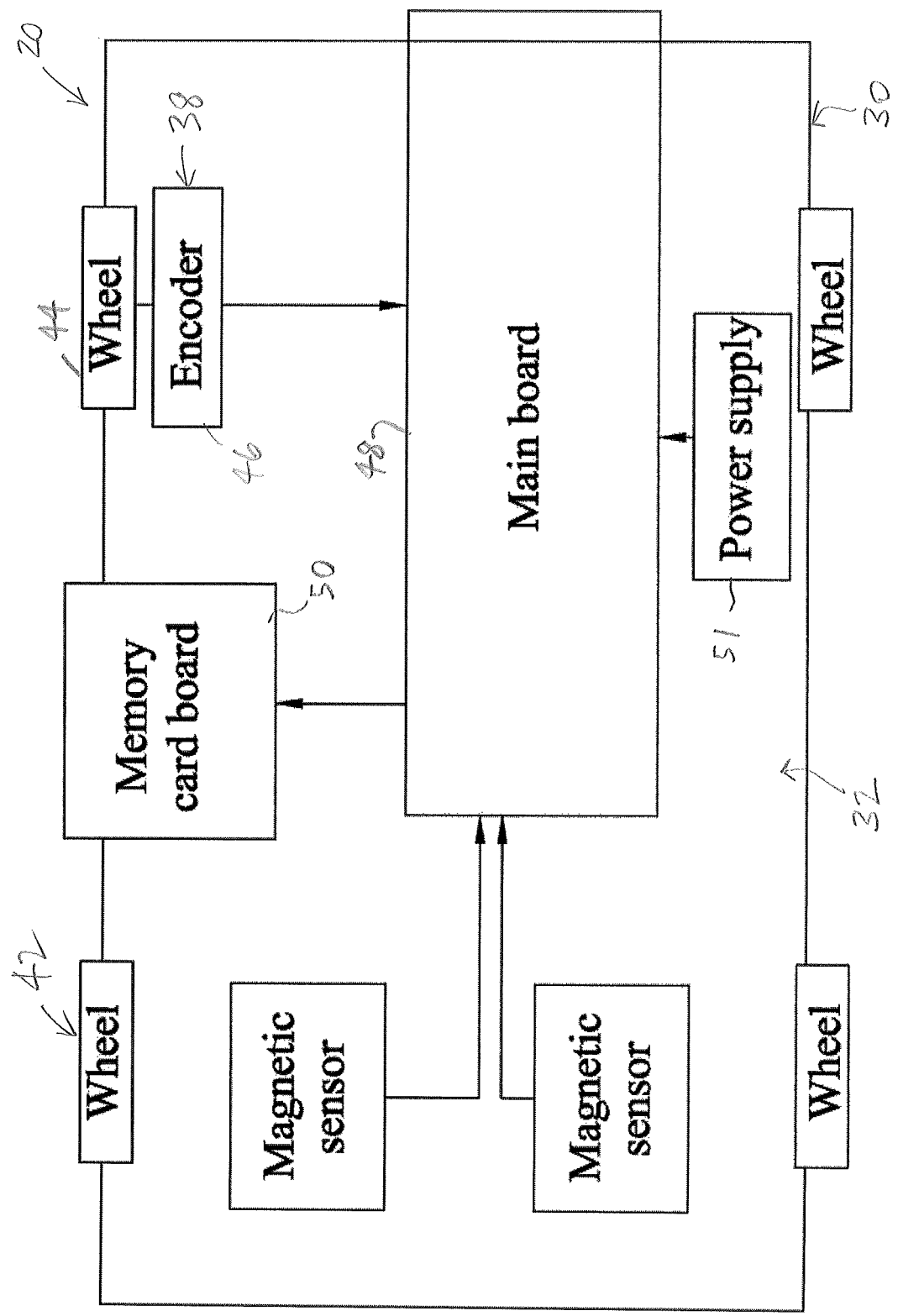
FIG. 5 is a block diagram of an embodiment of the sensor assembly of the invention.

In the attached drawings, like reference numerals designate corresponding elements throughout. Reference is first made to FIGS. 1-6 to describe an embodiment of a system of the invention indicated generally by the numeral 20 (FIG. 2A). As will be described, the system 20 is for determining whether a magnetic field associated with an elongate rebar element 22 that is at least partially positioned in a concrete body 24 of a reinforced structural element assembly 26 includes at least one anomaly 28. In one embodiment, the system 20 preferably includes a data-gathering unit 30 that includes a frame assembly 32 and a sensor assembly 34 (FIGS. 2B, 5). It is preferred that the frame assembly 32 is movable relative to the reinforced structural element assembly 26 in a preselected direction "D" along a preselected path "P" at a preselected velocity "V", as will also be described (FIG. 2B). It is also preferred that the sensor assembly 34 is mounted to the frame assembly 32, and the sensor assembly 34 includes one or more magnetic sensors 36 (FIG. 2B) for sensing at least part of the magnetic field as the sensor assembly 34 is moved relative to the concrete body 24, to generate magnetic field data defining magnetic flux density of the magnetic field of the rebar element 22.

In one embodiment, the system 20 preferably also includes one or more tracking assemblies 38 (FIG. 5) for generating location data to locate the magnetic field data relative to the concrete body 24. It is also preferred that the system 20 includes a processor 40 (FIG. 2A) for analyzing the magnetic field data for identifying the one or more anomalies, for analyzing the location data to locate the one or more anomalies relative to the concrete body 24, and for generating anomaly data describing the one or more anomalies. The location data and the magnetic field data are correlated to each other, to locate the anomaly relative to the concrete body in the anomaly data.

As can be seen in FIG. 2A, the system 20 preferably also includes a transportation assembly 42 for moving the data-gathering unit 30 relative to the concrete body 24 along the preselected path, to obtain the magnetic field data and the location data along a selected length "L" of the reinforced structural element assembly 26 (FIG. 2A).

In FIG. 2B, it can be seen that the preselected path "P" preferably is aligned with the rebar element 22. In particular, the preselected path "P" preferably is substantially aligned with a center line or axis "Q" of the rebar element 22 (FIG. 2B). In practice, the preselected path "P" preferably is laid out based on the relevant design dimensions of the reinforced structural element assembly 26. It will be understood that the rebar element 22 may not be directly viewable by an operator (not shown) of the data-gathering unit 30, and the preselected path "P" may be located, for example, based on measurements derived from the specifications of the reinforced structural element assembly 26. It is preferred that the data-gathering unit 30 is moved at the preselected velocity "V" along the preselected path "P". The direction "D" in which the data-gathering unit 30 is moved is consistent with the velocity "V".

Those skilled in the art would appreciate that the reinforced structural assembly 26, as illustrated, is exemplary only. It will be understood that, for the purposes hereof, the reinforced structural element assembly 26 and the concrete body 24 and the rebar element 22 thereof may have any suitable shape and size. The reinforced structural element assembly 26 is shown in FIG. 2A as having a simple form, i.e., elongate, with substantially flat surfaces "S" and the single elongate rebar element 22, to simplify the illustration. In practice, the rebar element 22 has a body that is generally in the form of an elongate solid cylinder, and the rebar element 22 usually includes ribs on the body.

Those skilled in the art would also appreciate that the reinforced structural element assembly 26 may include more than one rebar element 22. In such circumstances, the rebar elements 22 may be positioned substantially parallel to each other, and/or otherwise located relative to each other. For instance, some of the rebar elements 22 may cross others in the reinforced structural element assembly 26. It will be understood that the embodiments of the system and method disclosed herein may be applied in connection with the reinforced structural element assembly 26 that includes more than one rebar element 22.

It would be appreciated by those skilled in the art that the transportation assembly 42 may be provided in any suitable form, with any suitable elements. In one embodiment, the transportation assembly 42 preferably includes a number of wheels 44 that are operably mounted to the frame assembly 32 (FIG. 5). As can be seen in FIGS. 2A and 2B, it is preferred that the wheels 44 are engageable with the concrete body 24 and rotate as the data-gathering unit 30 moves relative to the concrete body 24 along the preselected path "P".

Those skilled in the art would appreciate that any suitable number of wheels may be used. In the embodiment illustrated, there are four wheels, identified for clarity of illustration by reference characters 44A-44D in FIG. 2B. Those skilled in the art would also appreciate that movement of the data-gathering unit 30 along the preselected path "P" may be caused and controlled by any suitable motive means (not shown).

Figure 1:
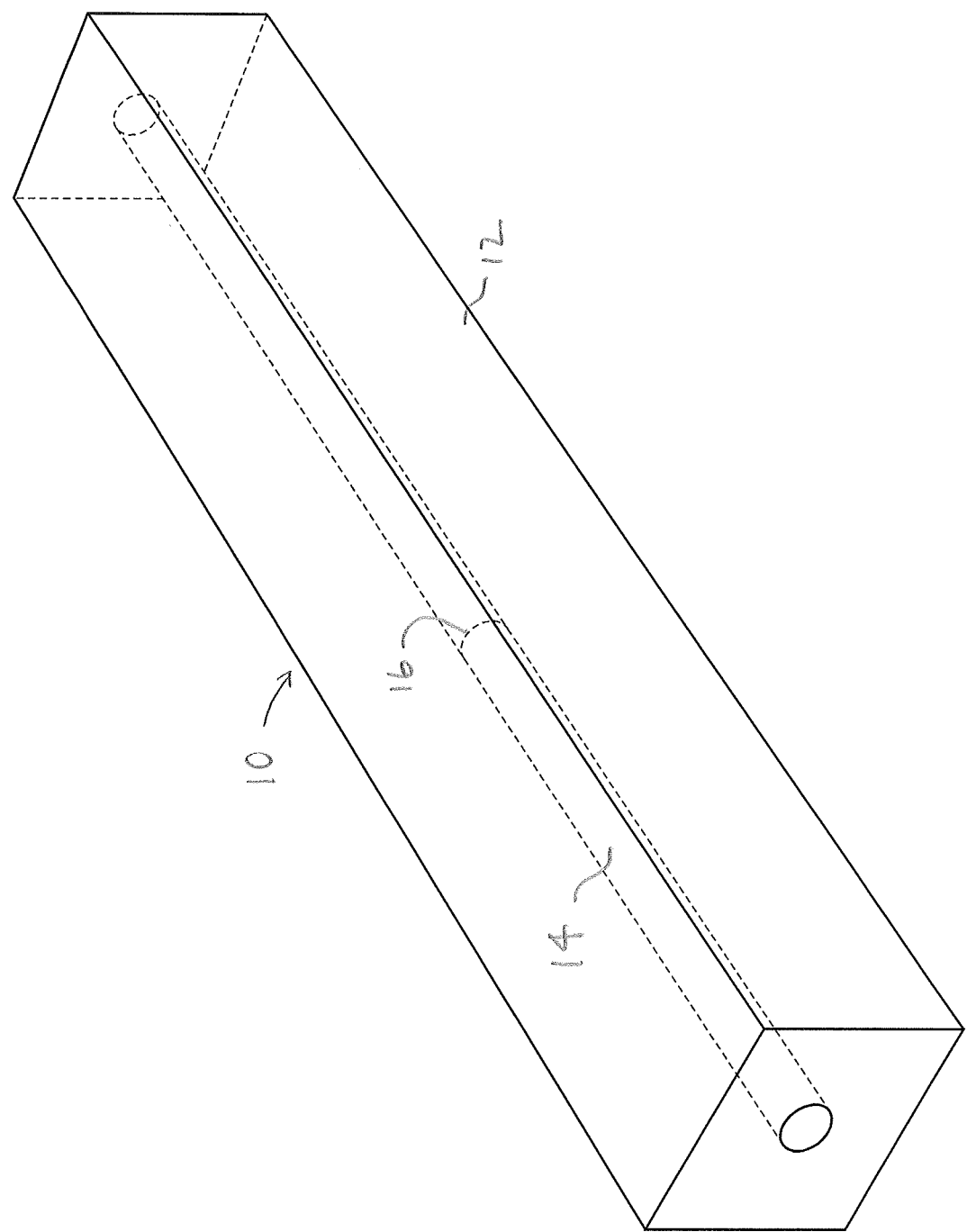
FIG. 1 (also described previously) is an isometric view of a reinforced concrete beam of the prior art.
Figure 2A:
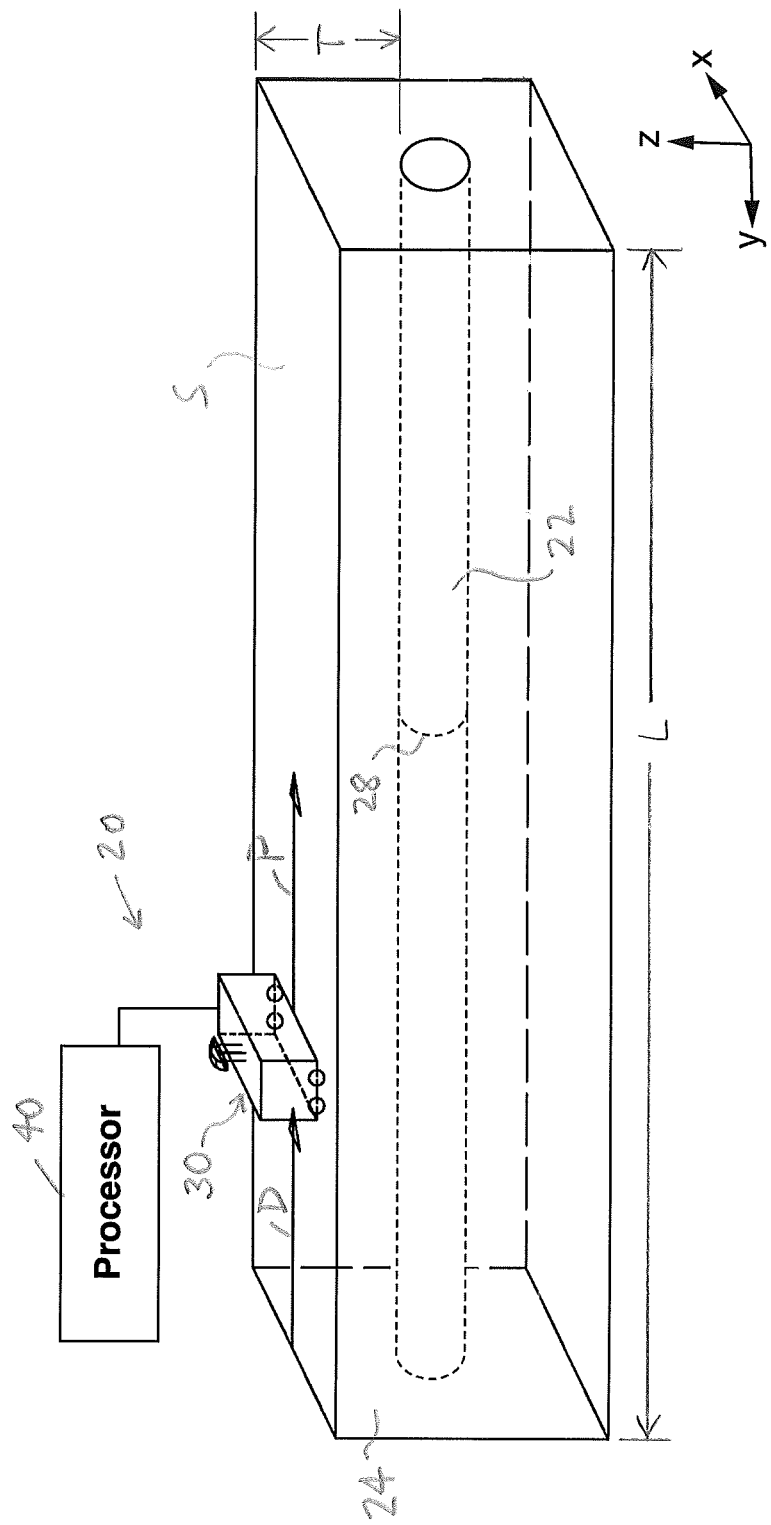
FIG. 2A is a schematic isometric illustration of an embodiment of a system of the invention, in which a data-gathering unit of the system is positioned on the reinforced structural element assembly.
Figure 2B:
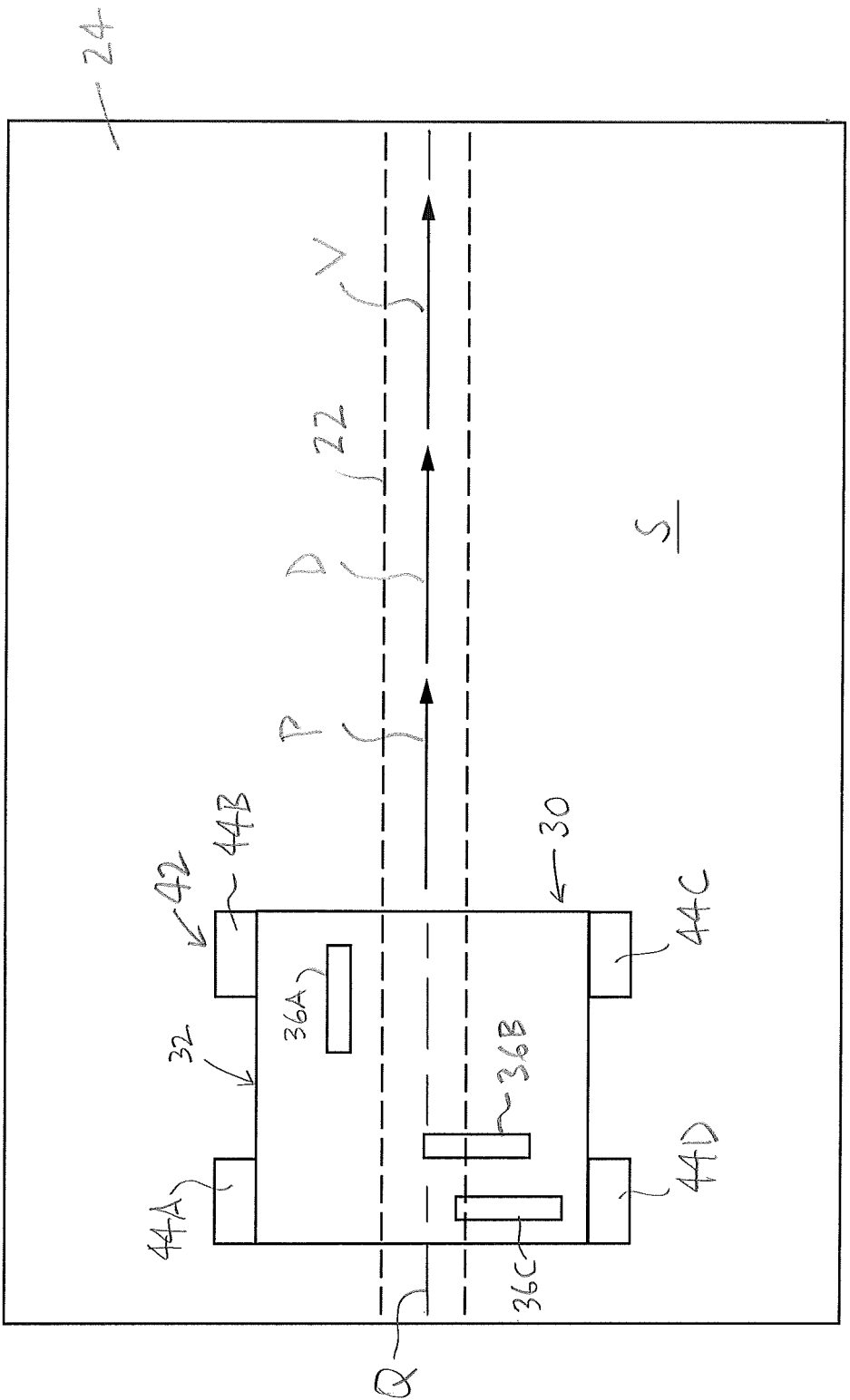
FIG. 2B is a schematic top view of the data-gathering unit of FIG. 2A positioned on the reinforced structural element assembly.
Figure 6:
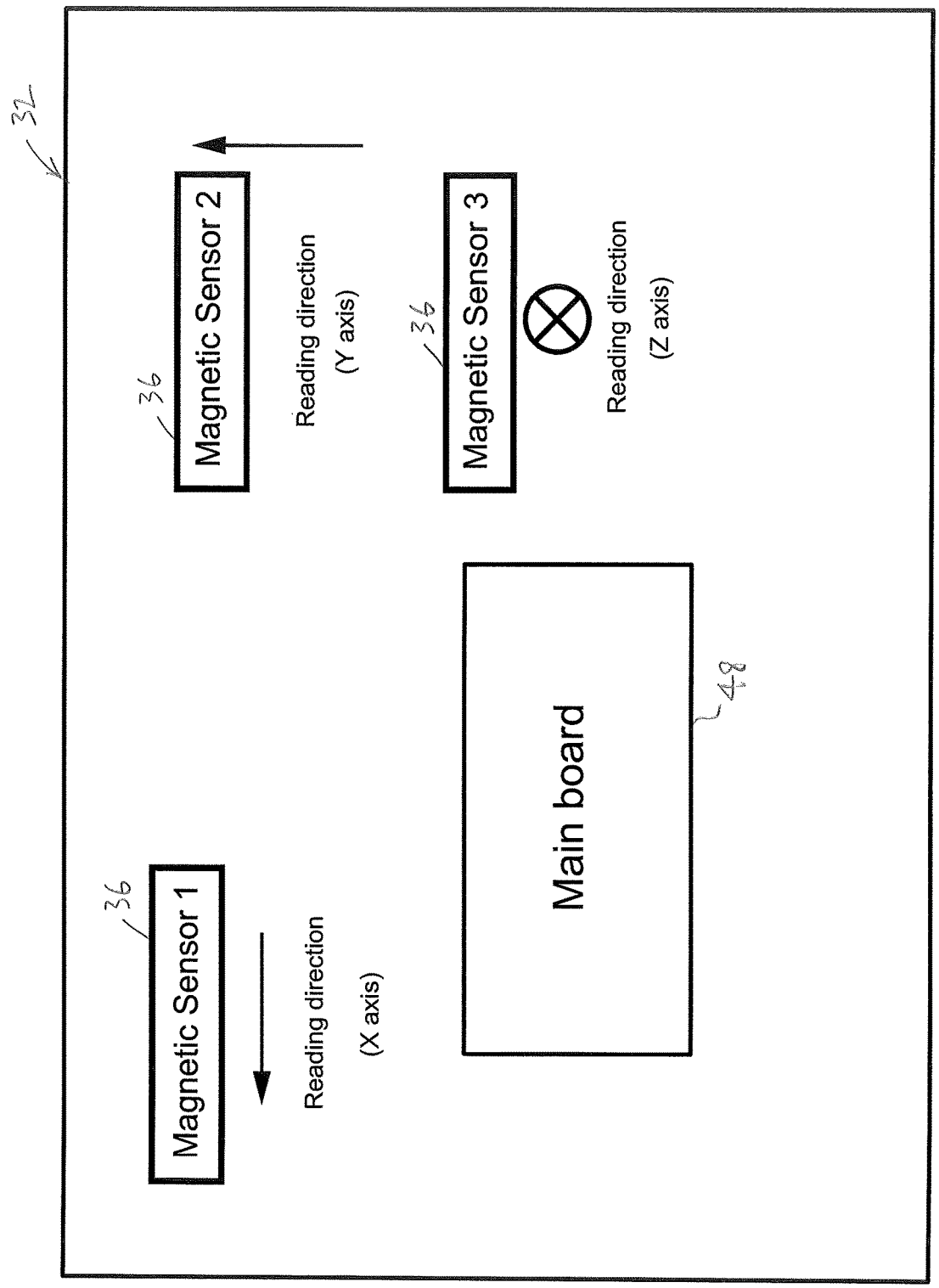
FIG. 6 is a block diagram of an alternative embodiment of the system of the invention.

As can be seen in FIGS. 1 and 2B, the rebar element 22 may be positioned in the concrete body 24 to extend along the concrete body's length "L". In FIG. 2A, three mutually orthogonal axes, "X", "Y", and "Z", are identified relative to the reinforced structural element assembly 26. As will be described, in one embodiment, the sensor assembly 34 preferably includes three magnetic sensors 36, each oriented to sense magnetic flux density along one of the axes "X", "Y", "Z" respectively (FIGS. 2B, 6). For example, in FIG. 6, the magnetic sensors 36 designated 1, 2, and 3 for convenience sense the magnetic field in the respective reading directions "X", "Y", and "Z".

Those skilled in the art would appreciate that the "X", "Y", and "Z" axes may be oriented relative to the rebar element 22 in any suitable manner. However, in practice, it has been found to be convenient to substantially align the "X" axis with the axis "Q" of the rebar element 22. In this orientation, the "Y" axis is orthogonal to the "X" axis, but in the same plane. Also, the "Z" axis preferably is orthogonal to the "X" axis, in a plane that is orthogonal to the plane of the "X" and "Y" axes.

It will be understood that the sensor assembly 34 may have any suitable configuration. As illustrated in FIGS. 2B, 5, and 6, in one embodiment, the sensor assembly 34 preferably is positioned on the frame assembly 32 (FIG. 5). The sensor assembly 34 preferably includes three magnetic sensors (identified in FIG. 2B for convenience by reference numbers 36A, 36B, and 36C). Those skilled in the art would be aware of suitable magnetic sensors. Preferably, the frame assembly 32 is supported by the wheels 44 (FIG. 5) that engage one of the surfaces "S" (FIG. 2) as the data-gathering unit 30 is moved along the concrete body 24, as will be described.

Those skilled in the art would appreciate that the tracking assembly 38 may include various means for locating the data-gathering unit 30 relative to the concrete body 24. In one embodiment, it is preferred that the tracking assembly includes one or more rotary encoders 46 (FIG. 5). Preferably, the rotary encoder 46 is operatively connected with at least a selected one of the wheels 44. The rotary encoder 46 preferably generates the location data based on the rotation of said selected one of the wheels 44 as the data-gathering unit 40 is moved along the preselected path "P" on the concrete body 24.

Figure 11:
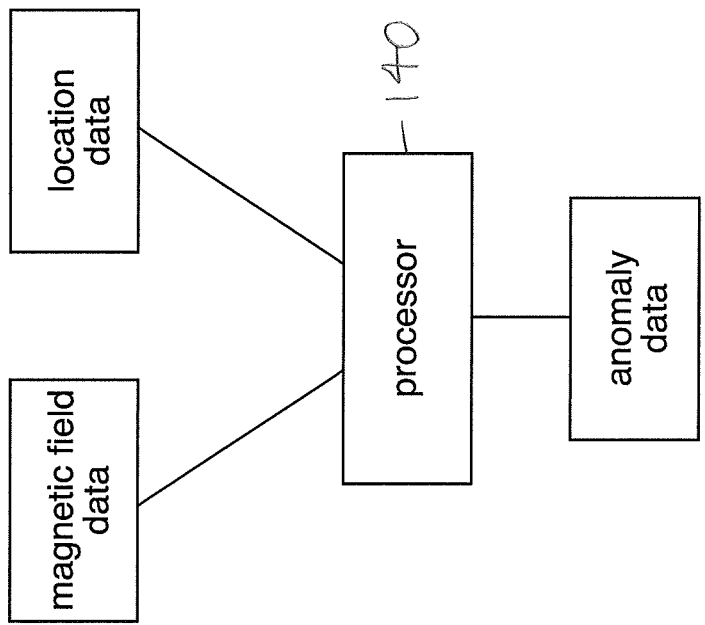
FIG. 11 is a block diagram illustrating an embodiment of the method of the invention.

It will be understood that the processor 40 may be positioned in the data-gathering unit 30, or the processor 40 may be positioned elsewhere. As described above, the magnetic field data and the location data preferably are transmitted to the processor 40, where the magnetic field data and the location data are processed to generate the anomaly data (FIG. 11).

For example, and as illustrated in FIG. 5, in one embodiment, the data-gathering unit 30 preferably also includes a main board 48 and a memory card board 50, for use with a memory card (not shown). Preferably, the magnetic sensors 36 and the memory card board 50 are all in communication with the main board 48. The main board 48 preferably has a suitable power source 51 (FIG. 5). It is also preferred that the main board 48 includes a pre-processor (not shown) programmed to synchronize the hardware and software of the sensor assembly 34. Those skilled in the art would also appreciate that the main board 48 preferably includes other elements (e.g., resistors and capacitors) to control input and output voltages of, e.g., the magnetic sensors 36, the rotary encoder 46, and the memory card board 50. Those skilled in the art would appreciate that the magnetic field data and the location data may be processed by the pre-processor. As will be described, for example, applying a high pass filter as a simple signal processing technique preferably is applied through the main board 48, before writing data into the memory card.

Those skilled in the art would appreciate that the data collected by the data-gathering unit 30 may be transmitted to the processor 40 in any suitable manner, using any suitable means. For instance, as described above, the data may be downloaded from the main board 48 onto a suitable device, which is then physically removed from the data-gathering unit 30 and electrically connected with the processor 40, for transmission of the data to the processor 40. Alternatively, in the absence of a memory card, the data may be transmitted from the data-gathering unit 30 to the processor 40, wirelessly or otherwise.

The three magnetic sensors 36A-36C preferably are mounted to the frame assembly 32 so that, when the data-gathering unit 30 is positioned on the reinforced structural element assembly 26 (i.e., with the wheels 44 engaging a selected one of the surfaces "S" of the concrete body 24), each of the magnetic sensors 36A-36C is substantially aligned with one of the axes "X", "Y", "Z" respectively.

The rotary encoder 46 preferably includes a portion thereof (not shown) formed for engagement with, and rotation with, a selected one of the wheels 44. Because of such engagement of the encoder 44, the position of the data-gathering unit 30 along the length "L" at any time may be known, and in particular, the locations at which the magnetic sensors 36A-36C detect anomalies can be related to locations in the concrete body 24.

Those skilled in the art would appreciate that the tracking assembly 38 and the sensor assembly 34 may be activated, and de-activated, in any suitable manner. It is preferred that the activation and de-activation of the tracking assembly 38 and the sensor assembly 34 permits relatively convenient, and consistent, correlation of the magnetic field data and the location data. In one embodiment, the tracking assembly 38 and the sensor assembly 34 preferably are activated on a time basis ("time mode") or on a location basis ("location mode").

In the time mode, the tracking assembly 38 (i.e., the rotary encoder 46) and the sensor assembly 34 (i.e., the magnetic sensors 36) may be activated at substantially the same time (a "start time"), and continue to generate the location data and the magnetic field data respectively until the collection of data thereby is ended, at substantially the same end time. When the tracking assembly 38 and the sensor assembly 34 operate in the time mode, the location data and the magnetic field data are correlated to each other on the basis of time, i.e., time that has elapsed from the start time.

Alternatively, the tracking assembly 38 and the sensor assembly 34 may be activated in the location mode. In the location mode, the tracking assembly 38 and the sensor assembly 34 are activated by movement of the data-gathering unit 30. Specifically, the activation is triggered by the rotary encoder(s) 46, when one or more of the wheels 44 begins rotating. While the tracking assembly 38 and the sensor assembly 34 are activated, they are generating the location data and the magnetic field data respectively. The tracking assembly 38 and the sensor assembly 34 preferably remain activated until the movement of the data-gathering unit 30 ceases, at which point they are de-activated.

When the tracking assembly 38 and the sensor assembly 34 operate in the location mode, the location data and the magnetic field data are correlated to each other on the basis of the location of the data-gathering unit 30 on the concrete body 24.

It will be understood that the time mode preferably is utilized where the surface "S", over which the data-gathering unit 30 is to travel, is relatively rough. In these circumstances, it is believed that the time mode is likely to result in more accurate data than the location mode.

The rebar element 22 is made of ferromagnetic material (e.g., steel), and has a magnetic field (referred to as a "stray magnetic field") associated with it, as will be described. Those skilled in the art would appreciate that there is also a background magnetic field that preferably is taken into account (described below). In addition, however, there may be an "ancillary" magnetic field in the region around the rebar element 22 that is associated with other ferromagnetic material(s) in the vicinity, and if so, then the ancillary magnetic field preferably is also taken into account. In general, the ancillary magnetic field is not as strong as the stray magnetic field.

The stray magnetic field is characteristic of the ferromagnetic body (i.e., the rebar element 22) itself. However, the ancillary magnetic field is a consequence of the Earth's magnetic field, modified by local magnetic bodies, if any. The magnetic flux density that is measurable in the vicinity of the rebar element 22 using passive techniques is related to these two magnetic fields. The background magnetic field is the Earth's magnetic field.

When the rebar element 22 is formed, its electrical dipoles in its crystalline structure are aligned with the Earth's, magnetic field or with a direction of applied mechanical stress (i.e., if applicable), resulting in induced magnetization. The self-magnetization of the rebar element 22 during its manufacture creates the stray magnetic field. It has been determined that irregularities in the rebar element 22 (e.g., holes in the rebar element, or roughened portions of the surface of the rebar) result in anomalies in the magnetic flux density of the stray magnetic field. It is believed that the irregularities cause variations in the magnetic flux density associated with the stray magnetic field.

In addition, the extent of the irregularity of irregular features of the rebar element can be reflected in corresponding quantitative aspects of the magnetic flux density.

However, as will be described further below, the anomalies in the magnetic flux density of the stray magnetic field of the rebar element 22, strictly speaking, are only indications of irregularities in the rebar element, i.e., the anomalies are only indications of physical features of the rebar element that are physically different from other portions of the rebar element. That is, the anomalies in the stray magnetic field correspond to irregularities in the rebar element, but what those irregularities are caused by cannot be known from the magnetic field data alone. However, it is believed that inferences may reasonably be made. The technique of the invention permits an inference to be made regarding corrosion of the rebar element, if it is assumed that all irregularities of the rebar element are due to corrosion. From the foregoing, it can be seen that the measurement of magnetic flux density of the stray magnetic field at known locations on the reinforced concrete assembly can provide indications of the extent of the corrosion of the rebar inside the reinforced concrete assembly.

However, as noted above, those skilled in the art would appreciate that there may be causes of the irregularities so identified, other than corrosion. That is, although the system 20 provides an indication of an irregularity in the rebar element, which indication may have a quantitative aspect, the nature of the irregularity is not confirmable via the system of the invention.

Concrete is a non-magnetic material with relative magnetic permeability of 1. Accordingly, the concrete body 24 has no effect on the magnetic flux density around the rebar element 22. This permits the method of non-destructive, and passive, testing described herein. Because of concrete's relative magnetic permeability, the magnetic flux density associated with the stray magnetic field of the rebar element 22 may be accurately sensed through the concrete body 24.

The system and the method described herein are considered "passive" because, in the invention herein, the measurement taken is a characteristic of a magnetic field. In making an "active" measurement, in contrast, something is done (e.g., passing an electric current through the rebar element 22, or vibrating the rebar element 22) that may affect the condition of the sample that is tested. It should be noted that even a very small change in the condition of the sample may be relevant, as even a small change in the sample may have a significant impact on the results. As a consequence, the results of active testing may be somewhat inaccurate. Also, when passive testing is utilized, repeated measurements or sensing of the same portion of the sample (to improve accuracy of the results) are possible.

Active testing generally involves two transmissions, i.e., an initial transmission to the sample (e.g., of electric current therethrough), and a subsequent return transmission from the sample. However, various environmental factors (e.g., relative humidity, temperature) may affect the transmission. Accordingly, active testing has the disadvantage that it typically involves two transmissions, and therefore it involves risks associated with environmental factors that may affect each of the two transmissions. In contrast, passive testing typically involves only one transmission.

For the foregoing reasons, it is believed that passive testing is generally preferably to active testing.

It will be understood that any suitable magnetic sensors may be used. Preferably, the magnetic sensors 36 are magneto-inductive sensors. However, those skilled in the art would be aware of other magnetic sensors (e.g., magnetic sensors utilizing the Hall effect) that would be suitable.

For the reasons set out above, it is preferred that the magnetic sensors 36 utilize a passive magnetic sensing method, e.g., they do not involve passing an electric current through the rebar element, or using similar methods to generate a magnetic field. In one embodiment, each magnetic sensor 36 preferably measures the magnetic field in two opposite directions, i.e., along each respective axis therefor. It is also preferred that each of the magnetic sensors measures the magnetic field at suitable rates, e.g., 10 to 100 measurements per second.

It is also preferred that magnetic data is obtained around the reinforced structural element assembly 26 in three dimensions (i.e., three mutually orthogonal directions). Accordingly, and as noted above, in one embodiment of the sensor assembly 28 of the invention, three magnetic sensors 36A, 36B, 36C preferably are used, each of which is positioned on one of three mutually orthogonal axes, such axes being identified as "X", "Y", and "Z".

Those skilled in the art would also appreciate that there is a limit to the distance that there may be between the magnetic sensor 36 and the ferromagnetic object (i.e., the rebar element 22) for effective sensing of the stray magnetic field. That is, if the distance between the magnetic sensor and the ferromagnetic sample is greater than a certain distance (depending primarily on the magnetic sensor), the magnetic sensor will not accurately sense the magnetic flux density of the magnetic field associated with the ferromagnetic sample (i.e., the rebar element 22).

In general, with the magneto-inductive sensors that are preferred, the maximum distance permissible between the sensor 36 and the rebar element 22 is approximately between 10 and 15 times the width (or diameter) of the ferromagnetic sample. For example, if the rebar element 22 has a nominal diameter (i.e., in its undamaged portions) of approximately 15 mm, then the sensor may be positioned up to between 15 cm to 22.5 cm apart from the ferromagnetic sample and still function properly.

Those skilled in the art would appreciate that each of the magnetic sensors preferably has a predetermined sensitivity to the magnetic field data. In addition, each of the magnetic sensors may have a different covering range respectively.

Those skilled in the art would appreciate that the rebar element 22 is required to be positioned in the reinforced structural element assembly 26 at a certain distance "T" from the adjacent surface "S" of the concrete body 24. In the reinforced concrete assembly 26, the distance "T" (FIGS. 2 and 4) permitted between the rebar element 22 and the surface "S" of the concrete body 24 is limited to approximately 7.62 cm (i.e., approximately 3 inches) in practice, in accordance with standard practice. Accordingly, because of this practical limit on concrete thickness in reinforced concrete, the sensors 36 located in the data-gathering unit 30 are positionable near the surface "S" in sufficient proximity to the rebar element 22 to permit the magnetic sensors 36 to accurately measure the magnetic flux density of the magnetic fields associated with the rebar element 22.

From the foregoing, it can be seen that the magnetic sensors 36 sense magnetic flux density associated with the stray magnetic field, and also that associated with the background magnetic field in the vicinity of the rebar element 22. It is preferred that the data gathered by the magnetic sensors 36 be processed (via a signal processing methodology developed for the purpose) to subtract or filter background magnetic field trend (i.e., magnetic flux density associated with the background magnetic field), for extracting signal anomalies that indicate corrosion of the rebar element.

It has been determined that the raw magnetic flux density data shows two different trends, i.e., both low and high frequencies are found in the signal. It is also known that natural (external) magnetic fields are spatially variable, giving a low-frequency trend. In one embodiment, a high pass filter is therefore applied to attenuate the low frequency trend from the raw data. Those skilled in the art would appreciate that the appropriate filtering parameters preferably are determined via a frequency spectrum analysis.

Because the details of the frequency spectrum analysis may vary depending on location, it is also preferred that the system 20 is calibrated before a particular sample of the reinforced structural element assembly 26 is tested. As noted above, the calibration may be in respect of the background magnetic field only. However, if another ferromagnetic body is located in the vicinity of the reinforced structural element assembly, there may also be an ancillary magnetic field that also needs to be taken into account. This is believed to be necessary in order to ensure that the filtering parameters used are appropriate for the specific sample that is to be tested. As noted above, it is preferred that the sample 26 is tested in situ.

Preferably, during calibration of the system, the presence and value of the magnetic field of the Earth in the location of interest (i.e., the background magnetic field) is evaluated. It is also preferred that the system is calibrated accordingly, to confirm its accuracy.

Figure 13:
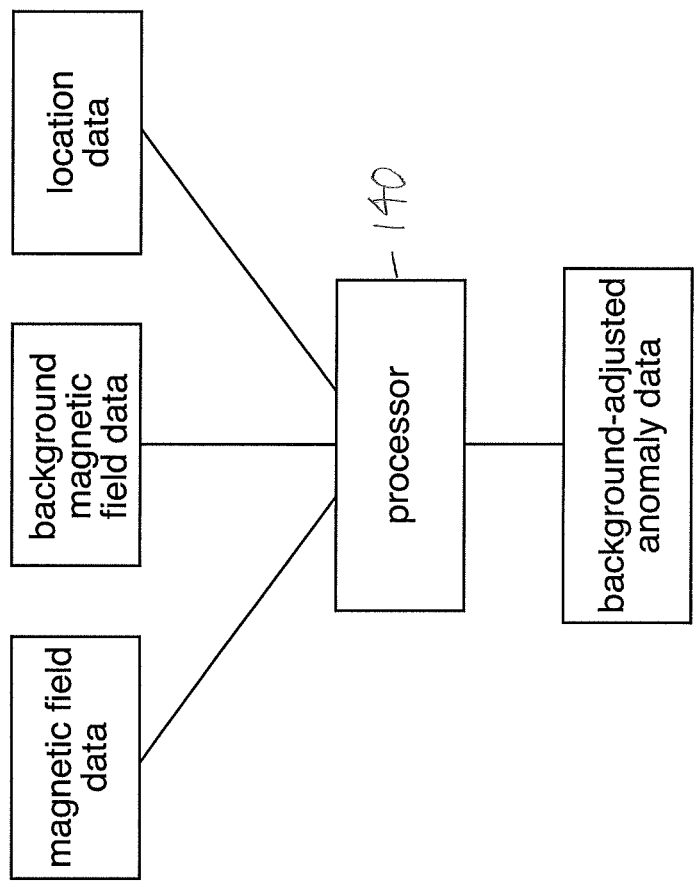
FIG. 13 is a block diagram illustrating another embodiment of the method of the invention.

In one embodiment, the magnetic sensor 36 preferably is configured to sense at least part of a background magnetic field proximal to the reinforced structural element assembly 26, to generate background magnetic field data defining background magnetic flux density of the background magnetic field. It is preferred that the processor 40 is configured for analyzing the background magnetic field data, to calibrate the processor 40 so that the background magnetic field data is taken into account to provide background-adjusted anomaly data. The utilization of the magnetic field data, the location data, and the background magnetic field data to provide the background-adjusted anomaly data is schematically illustrated in FIG. 13.

In one embodiment, the calibration process preferably involves recording the magnetic flux density of the magnetic fields in an area proximal to the sample reinforced concrete assembly to be tested in three different mutually orthogonal directions ("X", "Y", and "Z"). This provides the appropriate filtering parameters for the sample reinforced structural element assembly 26 that is to be tested. The values thus obtained may then be, in effect, subtracted from the recorded test data (i.e., filtered) for the sample reinforced structural element assembly 26, as described above.

From the foregoing, it can be seen that, in order to test a particular sample reinforced structural element assembly 26, the sensor assembly 34 preferably is utilized to obtain data about the background magnetic field in an area proximal to the sample 26, for calibration purposes. Once obtained, such data is transmitted to the processor 40 for processing, as described above.

After calibration, the data-gathering unit 30 preferably is then moved along the surface "S" of the concrete body 24 of the sample 26, to obtain raw magnetic field data (i.e., magnetic flux density) in respect of the sample reinforced structural element assembly 26, and the location data. As an example, in FIG. 2, the sensor assembly 28 is moved relative to the reinforced concrete assembly 26 in the direction indicated by arrow "D". The raw magnetic field data thus obtained is transmitted to the processor 40 in any suitable manner. Also, the location data is transmitted to the processor 40. The raw magnetic field data is then processed by the processor 40 to provide the magnetic flux density associated with the stray magnetic field of the rebar element, in order to determine whether there are anomalies therein.

The location data from the rotary encoder 46 is also transmitted to the processor 40, in any suitable manner. It will be understood that the location data provided by the rotary encoder 46 is paired or correlated with the raw magnetic field data, to locate the raw magnetic field data relative to the concrete body 24, i.e., relative to the length "L" thereof. In general, the rebar element 22 has a length that is coincident with and equal to "L" (e.g., as illustrated in FIG. 4), and the location data therefore also locates the raw magnetic field data relative to the rebar element 22.

The result of the processing of the magnetic field data and the location data described above is referred to herein as "the anomaly data".

As noted above, in one embodiment, due to the initial calibration step, the raw magnetic field data preferably is filtered by the processor 40 so that the modified magnetic field data remaining thereafter is related to the magnetic flux density associated with the stray magnetic field of the rebar element 22. For example, if the calibration has been in respect of the background magnetic field only, the result of the processing is referred to herein as "the background-adjusted anomaly data".

Figure 3:
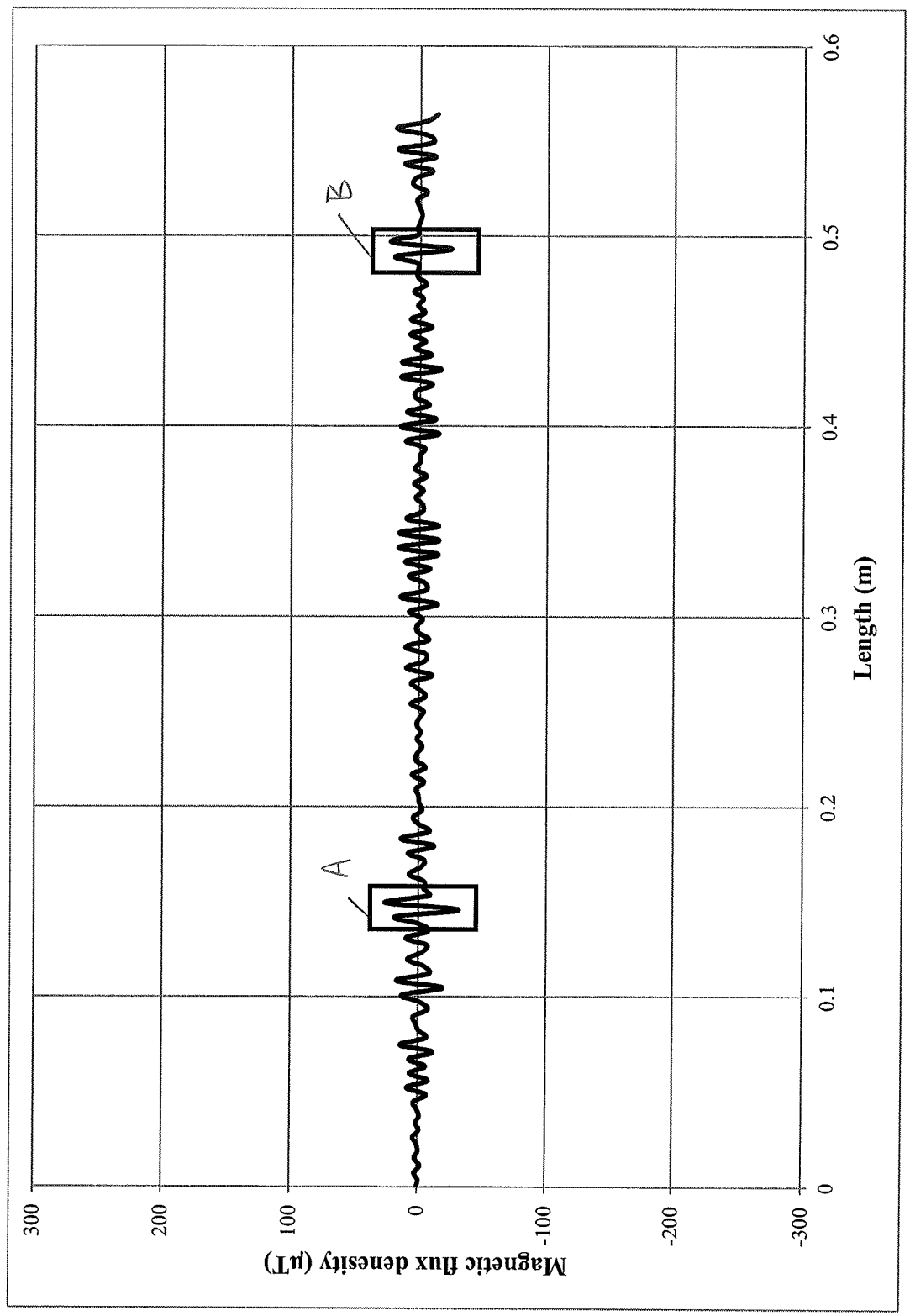
FIG. 3 is a graph in which the magnetic flux density associated with a rebar element is shown as including two anomalies.

An example of a plot of the magnetic flux density associated with a stray magnetic field of the rebar element 22 of the sample reinforced structural element assembly 26 is provided in FIG. 3. (It will be understood that, in the sample illustrated, the length "L" of the concrete body 24 is substantially coincident with the length of the rebar element 22.) As can be seen in FIG. 3, in this sample, the magnetic flux density is substantially the same along the length of the rebar element 22, with only two exceptions. At two locations (identified for convenience as "A" and "B" respectively in FIG. 3, and in the graph portion of FIG. 4), there is substantially higher magnetic flux density, i.e., there are two anomalies in the example illustrated in FIG. 3, and in the graph portion of FIG. 4. As noted above, the anomalies are indicative of irregularities in the rebar element 22.

In the normal course, absent information to the contrary, it is reasonable to assume that the irregularities indicated by the anomalies are caused by corrosion. However, it will be understood that any sort of irregularity in the rebar element 22 (e.g., a hole, or a cut in the rebar element, that is not formed due to corrosion, but is instead formed in some other way) may result in an anomaly in the magnetic flux density. Accordingly, in general, in the absence of information to the contrary, the rebar element 22 is assumed to be substantially free from holes, cuts, scratches, and similar irregularities.

As noted above, due to the rotary encoder 46, the data provided by the magnetic sensor 36 can be related to specific locations along the length "L" of the concrete body 24, and therefore also to corresponding locations along the length of the rebar element 22 therein. This can be seen in FIG. 4, in which the graph of FIG. 3 is reproduced, with a cross-section of the sample reinforced structural element assembly 26 positioned adjacent to the graph. The cross-section of the sample 26 is drawn in FIG. 4 so that it corresponds to the graph of FIG. 4, i.e., the length "L" of the concrete body 24 of the sample is the same in the cross-section and in the graph portion of FIG. 4, and the ends of the graph plot and the length "L" are aligned.

In the cross-section of FIG. 4, two regions of corrosion of the rebar element 22, identified by reference numerals 52 and 54 respectively for clarity of illustration, are shown. The anomalies "A" and "B" in the graph correspond to the corroded regions 52 and 54 in the cross-section of FIG. 4 respectively. As can be seen in FIG. 4, the locations of the areas of corrosion 52, 54 can be reliably determined from the graph. It will also be understood that, as described above, the extent of the magnetic flux density in the anomalies "A" and "B" in the graph of FIG. 4 correlates to the extent of the irregularities of the rebar element in its corroded regions 52, 54. Depending on the circumstances, therefore, a relatively high magnetic flux density anomaly may be indicative of a relatively severely corroded portion of the rebar element 22.

In one embodiment, the invention includes a method for determining whether the magnetic field associated with the rebar element 22 that is at least partially positioned in the concrete body 24 includes one or more anomalies. Preferably, the method includes providing one or more magnetic sensors 36, for sensing at least part of the magnetic field, and moving the data-gathering unit 30 including the magnetic sensor(s) 36 relative to the reinforced structural element assembly 26, to generate data defining magnetic flux density of the magnetic field of the rebar element 22. With one or more tracking assemblies 38, location data is also generated as the data-gathering unit is moved on the concrete body, to locate the magnetic field data relative to the concrete body 24. The magnetic field data and the location data is transmitted to the processor 40. With the processor 40, the data is analyzed, to identify any anomaly, and for analyzing the location data, to locate any such anomaly relative to the concrete body 24. As described above, it is preferred that the data-gathering unit 30 is moved by the transportation assembly 42.

As noted above, it is preferred that the background magnetic field is taken into account. The method preferably includes, with the magnetic sensor(s), sensing at least part of the background magnetic field proximal to the reinforced structural element assembly, to generate background magnetic field data defining background magnetic flux density of the background magnetic field. It is also preferred that, with the processor, the anomaly data is adjusted in view of the background magnetic field data, to provide background-adjusted anomaly data.

In one embodiment, the magnetic sensor 36 preferably is configured for sensing the magnetic field in X, Y, and Z directions. As described above, the X, Y, and Z directions are mutually orthogonal. Accordingly, the magnetic field data related to the magnetic field that is obtained by the magnetic sensor 36 preferably includes X, Y, and Z magnetic field data. Those skilled in the art would appreciate that the X, Y, and Z magnetic field data includes measurements of the magnetic flux density in the vicinity of the rebar element 22 in the X, Y, and Z directions respectively.

Figure 7:
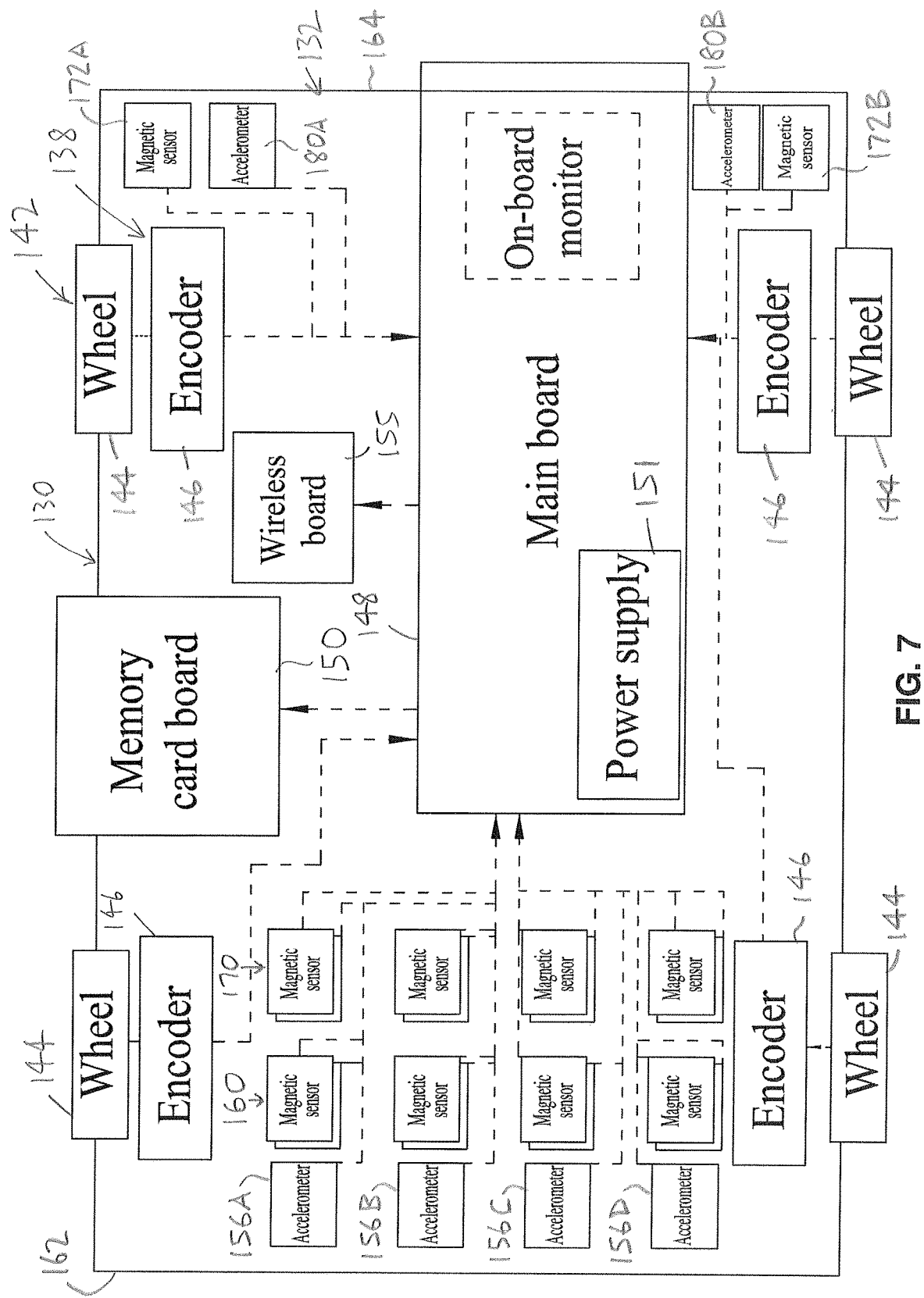
FIG. 7 is a block diagram of another alternative embodiment of the system of the invention.
Figure 8A:
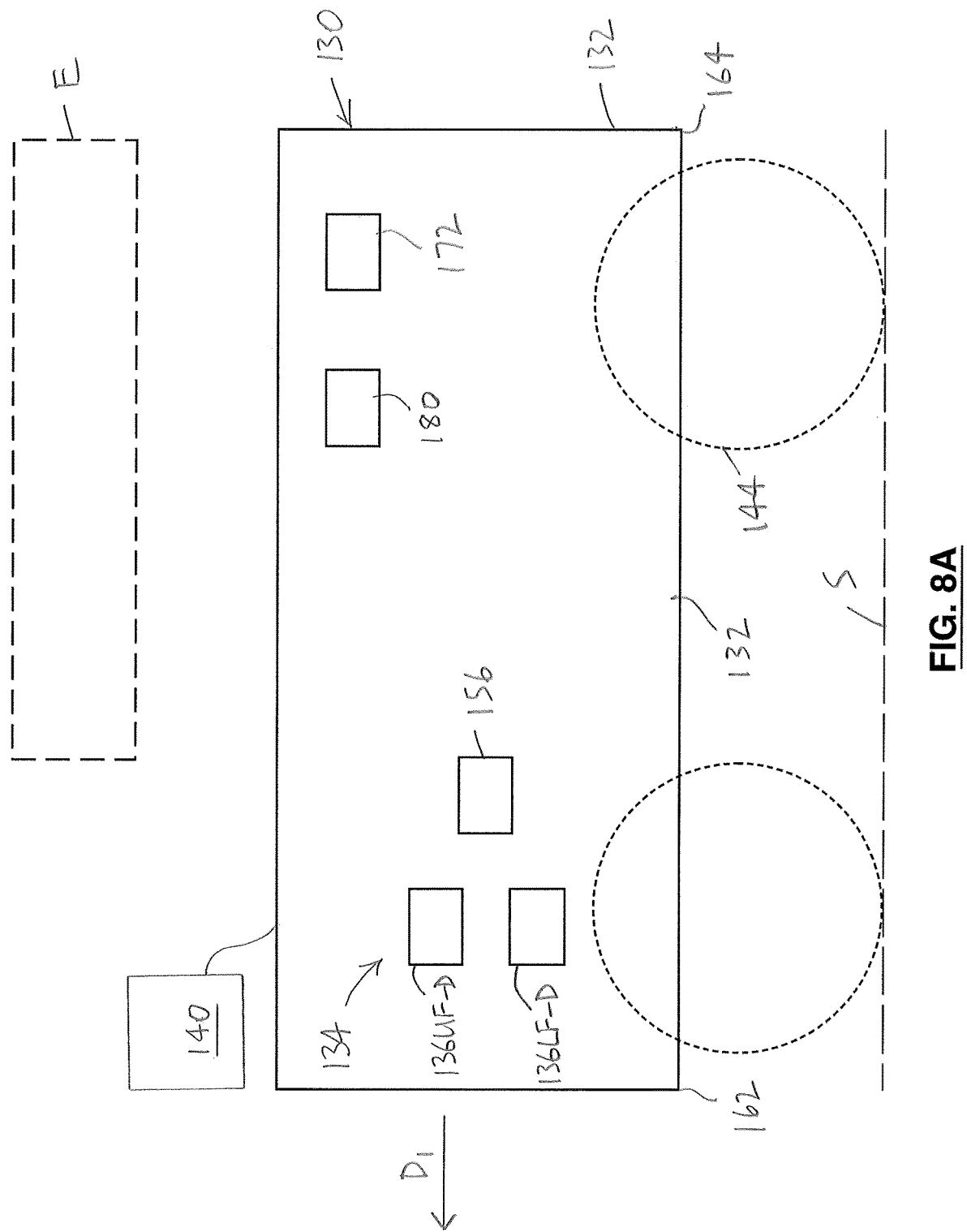
FIG. 8A is a schematic side view of an embodiment of a data-gathering unit of the invention included in the system of FIG. 7.
Figure 8B:
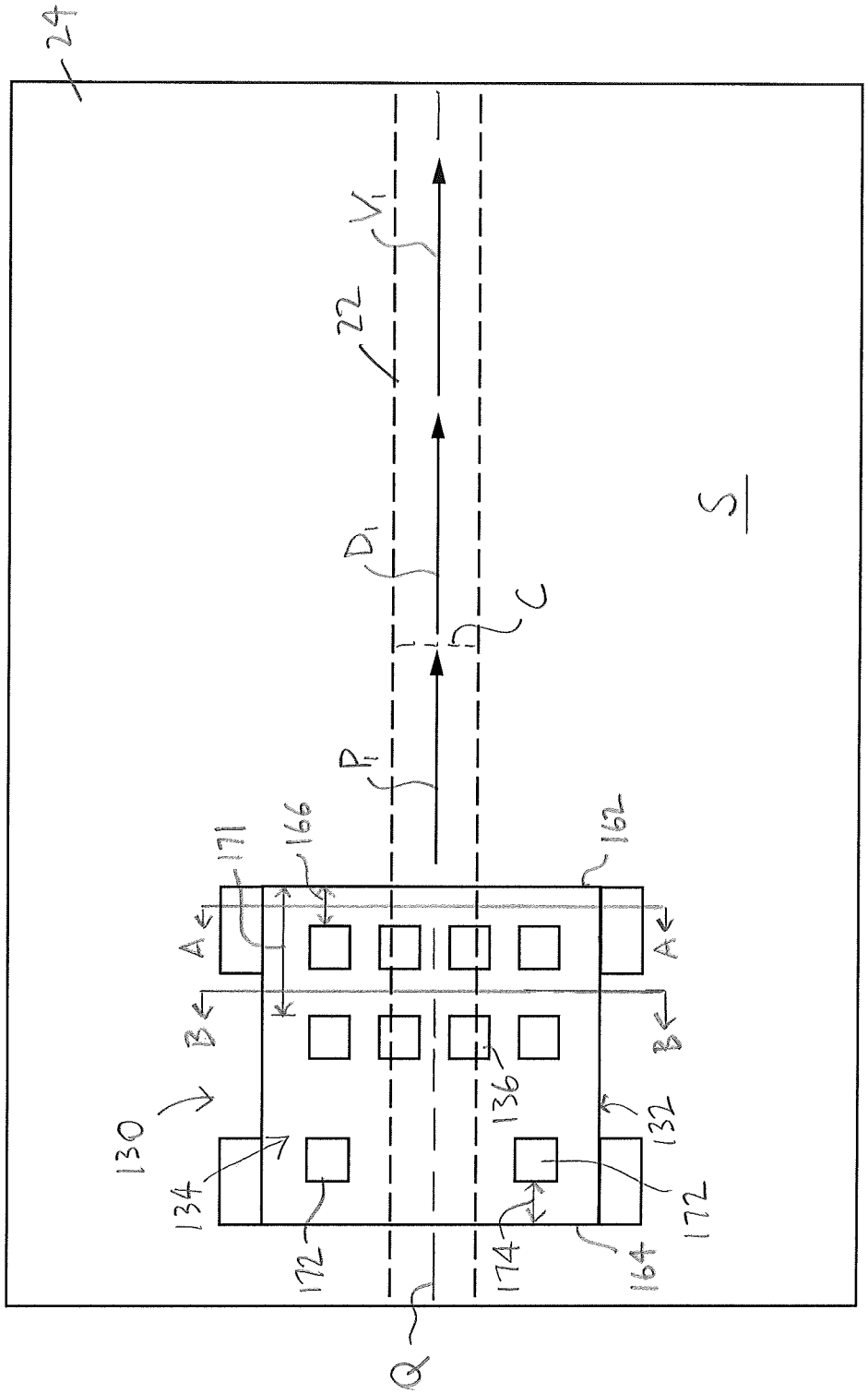
FIG. 8B is a schematic top view of the data-gathering unit of FIG. 8A positioned on the reinforced structural element assembly.

An alternative embodiment of a system 120 is illustrated in FIGS. 7-10. The system 120 (FIG. 8A) preferably includes a sensor assembly 134 including a number of magnetic sensors 136 mounted to the frame assembly 132, as will be described. The sensor assembly 134 and the frame assembly 132 preferably are included in a data-gathering unit 130 (FIGS. 7-8B).

As can be seen in FIG. 7, the system 120 preferably includes a tracking assembly 138 and a transportation assembly 142, as well as a processor 140. Preferably, the transportation assembly 142 includes a number of wheels 144 that are mounted to the frame assembly 132, to support the frame assembly 132 above the surface "S" of the concrete body 24. The tracking assembly 138 preferably also includes a number of rotary encoders 146 operably connected with the wheels 144, to provide the location data.

As can also be seen in FIG. 7, the data-gathering unit 130 preferably includes a main board 148 that includes a power source 151, and a memory card board 150.

In one embodiment, the data-gathering unit 130 preferably also includes a board 155 (FIG. 7) that permits the data gathered by the data-gathering unit 130 to be transmitted wirelessly, e.g., to a Bluetooth-enabled device, or otherwise transmitted wirelessly.

It is also preferred that the main board 148 includes an on-board monitor (FIG. 7). The on-board monitor may provide information to an operator (not shown) in real time, which may be used by the operator as the data-gathering unit 130 is moved along a preselected path "$P_1$". For example, if the operator observes a particularly large or strong anomaly, the operator may physically mark the concrete body at the point thereon, while the data-gathering unit is at the location in question.

As can be seen in FIG. 8B, the data-gathering unit 130 preferably is moved along the preselected path "$P_1$" in a preselected direction "$D_1$" at a preselected velocity "$V_1$". The preselected path "$P_1$" is substantially aligned with a center line or axis "$Q_1$" of the rebar element 22. It is preferred that the preselected path "$P_1$" is substantially aligned with a center line of the rebar element 22.

Figure 12:
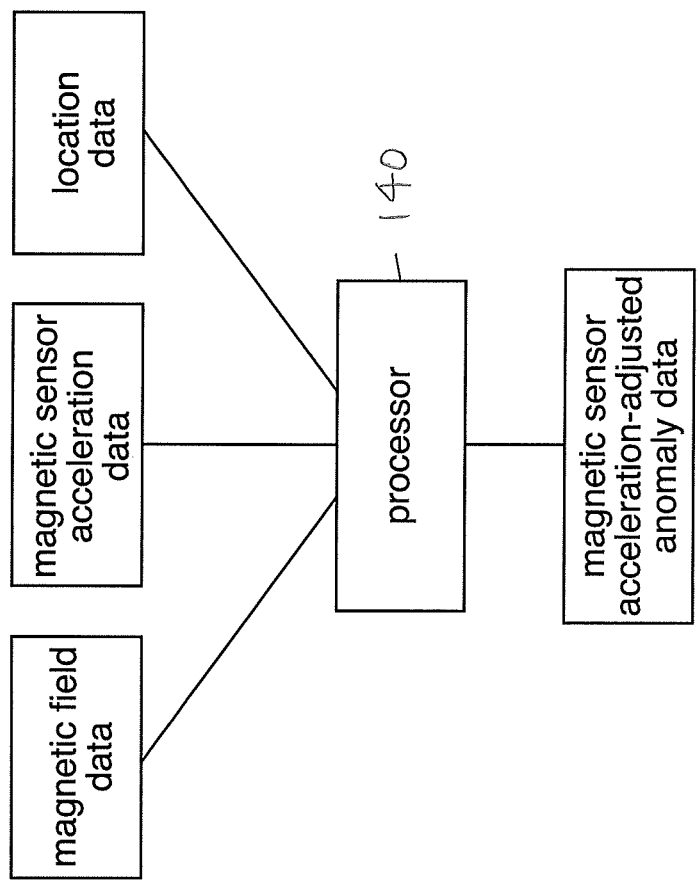
FIG. 12 is a block diagram illustrating another embodiment of the method of the invention.

In one embodiment, the sensor assembly 134 of the invention preferably includes one or more accelerometer(s) 156 (FIG. 8A) mounted to the frame assembly 132 and located in a predetermined position relative to one or more of the magnetic sensors 136, for sensing one or more accelerations of the magnetic sensor(s) 136. Such an acceleration causes the magnetic sensor(s) 136 to move relative to the concrete body 24 (not shown in FIGS. 7-10) at one or more modified velocities that differ from the preselected velocity. The accelerometer 156 is configured to provide magnetic sensor acceleration data related to the acceleration(s) transmittable to a processor 140 (FIG. 8A) of the system 120. Preferably, the processor 140 is configured for adjusting the anomaly data in view of the magnetic sensor acceleration data to provide magnetic sensor acceleration-adjusted anomaly data. The utilization in the processor 140 of the magnetic field data, the location data, and the magnetic sensor acceleration data to provide the magnetic sensor acceleration-adjusted anomaly data is schematically illustrated in FIG. 12.

Figure 14:
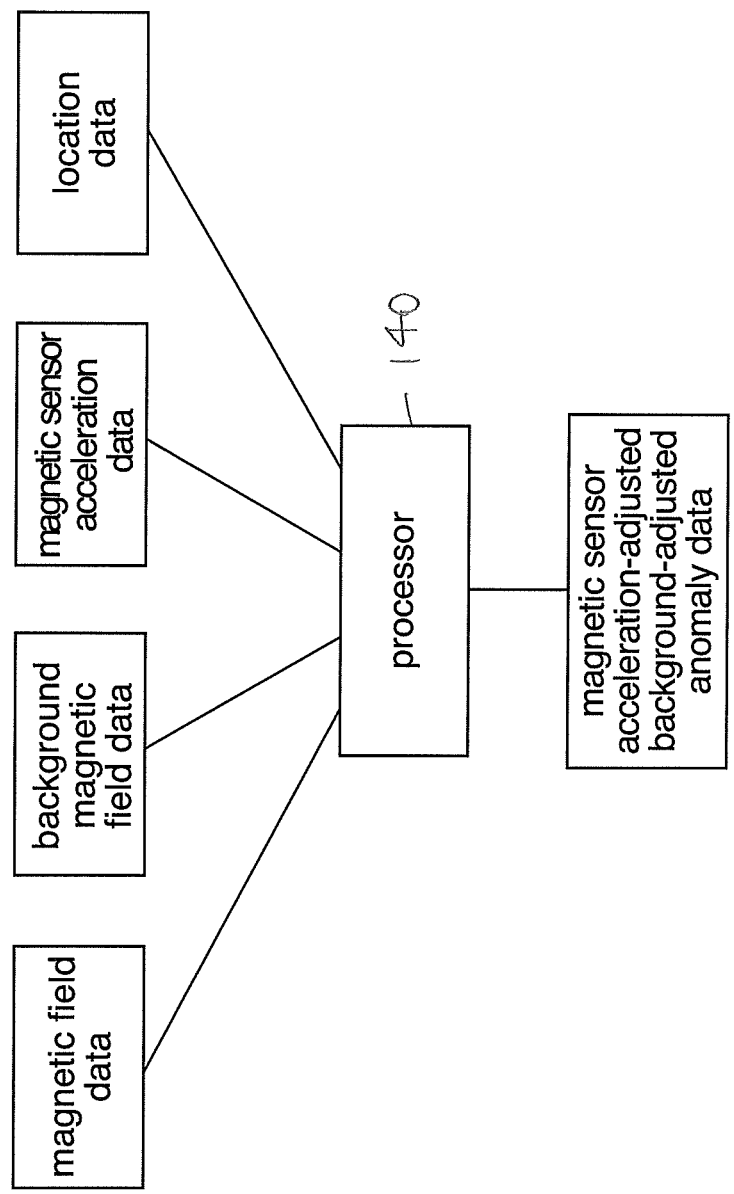
FIG. 14 is a block diagram illustrating another embodiment of the method of the invention.

It will be understood that the magnetic sensor acceleration data and the background magnetic field data may both be utilized. The utilization in the processor 140 of the magnetic field data, the location data, the magnetic sensor acceleration data, and the background magnetic field data to provide magnetic sensor acceleration-adjusted, background-adjusted anomaly data is schematically illustrated in FIG. 14.

It will be understood that the accelerometers 156 are included in the sensor assembly 134 in order to provide more accurate data about the anomalies (if any) in the magnetic field) associated with the rebar element 22. The predetermined position in which a particular accelerometer is located preferably is proximal to the one or more magnetic sensors about which the accelerometer is to provide the magnetic sensor acceleration data. Those skilled in the art would appreciate that the magnetic sensor acceleration data is initially transmitted to the main board 148, independent of the magnetic field data that is provided by the magnetic sensors 136.

Those skilled in the art would appreciate that the preselected velocity "$V_1$" is a vector (i.e., velocity involves movement in a direction at a speed). Those skilled in the art would also appreciate that, for the purposes hereof, "acceleration" of the magnetic sensor 136 that is moving at the preselected velocity may include increase or decrease of a speed, and "acceleration" also may include any change in direction of travel of the magnetic sensor 136. Because the magnetic sensor 136 is mounted to the frame assembly 132, acceleration of the data-gathering unit 130 is approximately the same as acceleration of one of the magnetic sensors 136. However, and as will be described, for greater accuracy in the magnetic sensor acceleration data, it is preferred that a number of the accelerometers 156 be included in the data-gathering unit 130, positioned proximal to the magnetic sensors 136 respectively. It will be understood that the modified velocity "$V_1$" differs from the preselected velocity as a result of the acceleration to which the magnetic sensor 136 is subjected.

For instance, as a data-gathering unit 130 (FIGS. 8A, 8B) is moved along the preselected path "$P_1$", the magnetic sensors 136 may be redirected (i.e., temporarily or otherwise), or the velocity of the magnetic sensors 136 may be otherwise changed (e.g., the speed may be decreased, or increased). For example, if the data-gathering unit 130 encounters an obstacle on the surface "S" (e.g., a bump, or irregularity) when moving along the preselected path "$P_1$" that causes a sudden movement of the data-gathering unit 130, the data-gathering unit 130 and the sensor assembly 134 therein are subjected to acceleration resulting therefrom. Accordingly, the preselected velocity of the magnetic sensors 136 therein is changed by the acceleration, i.e., to provide the modified velocity. Such changes in the velocity of the magnetic sensor 136 adversely affect the magnetic field data obtained thereby, because any acceleration of a magnetic sensor 134 affects the accuracy of the magnetic field data that is sensed by the magnetic sensor 134 during its acceleration. The extent to which any individual ones of the magnetic sensors is accelerated may vary relative to others, depending on, among other things, the position thereof in the data-gathering unit. Accordingly, it is believed that the acceleration to which each of the magnetic sensors is subjected respectively may be different, if only to a very small extent. The processor 140 is configured to determine the magnetic sensor acceleration-adjusted anomaly data, in which adjustments have been made to take the acceleration of the magnetic sensor(s) 136 (as detected by the accelerometer(s) 156) into account.

Those skilled in the art would appreciate that, after the data-gathering unit 130 has moved at the modified velocity, it may subsequently move again at the preselected velocity "$V_1$".

Figure 9A:
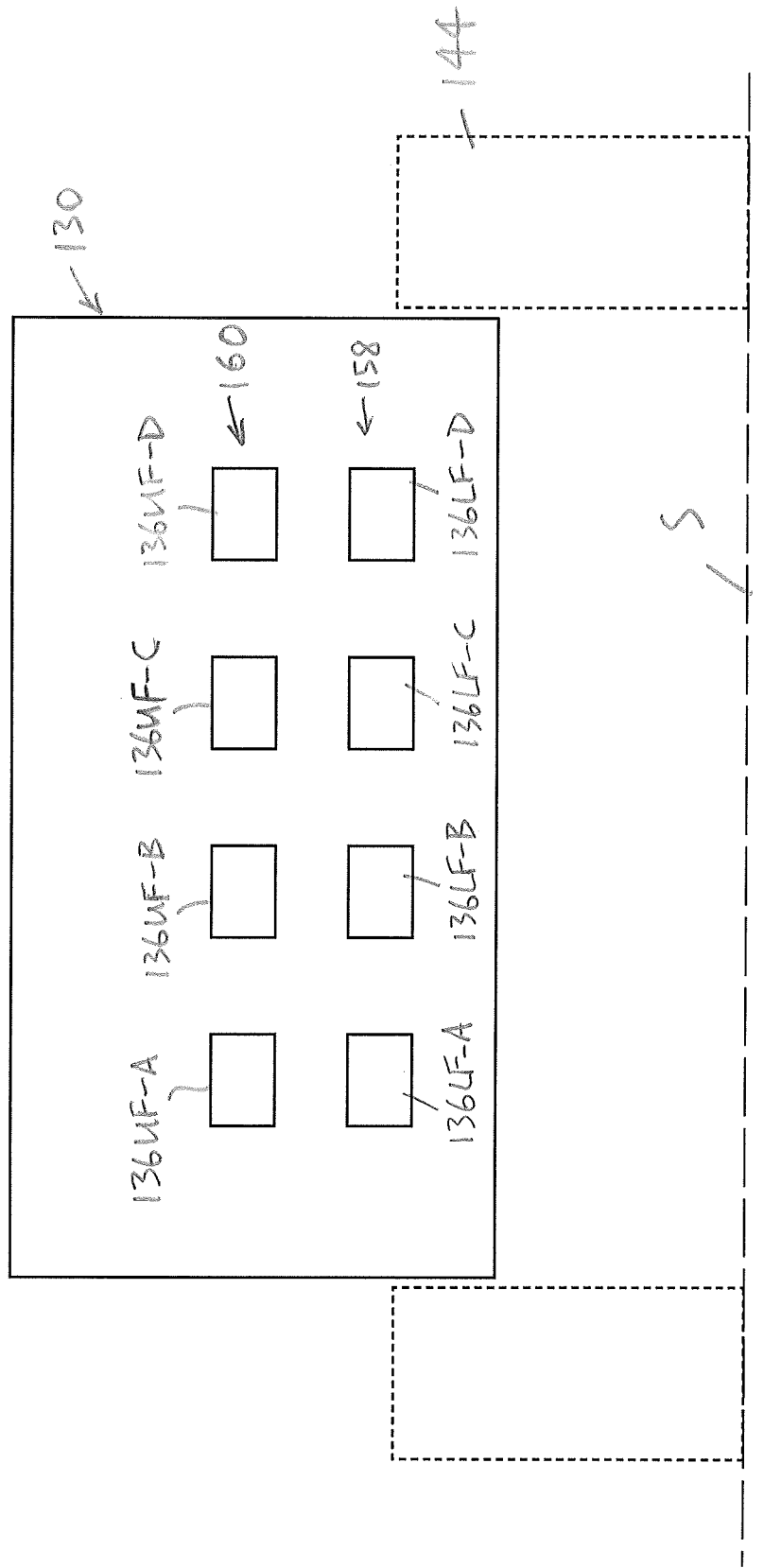
FIG. 9A is a schematic partial cross-section of the data-gathering unit of FIG. 8A, taken along line A-A in FIG. 8B.
Figure 9B:
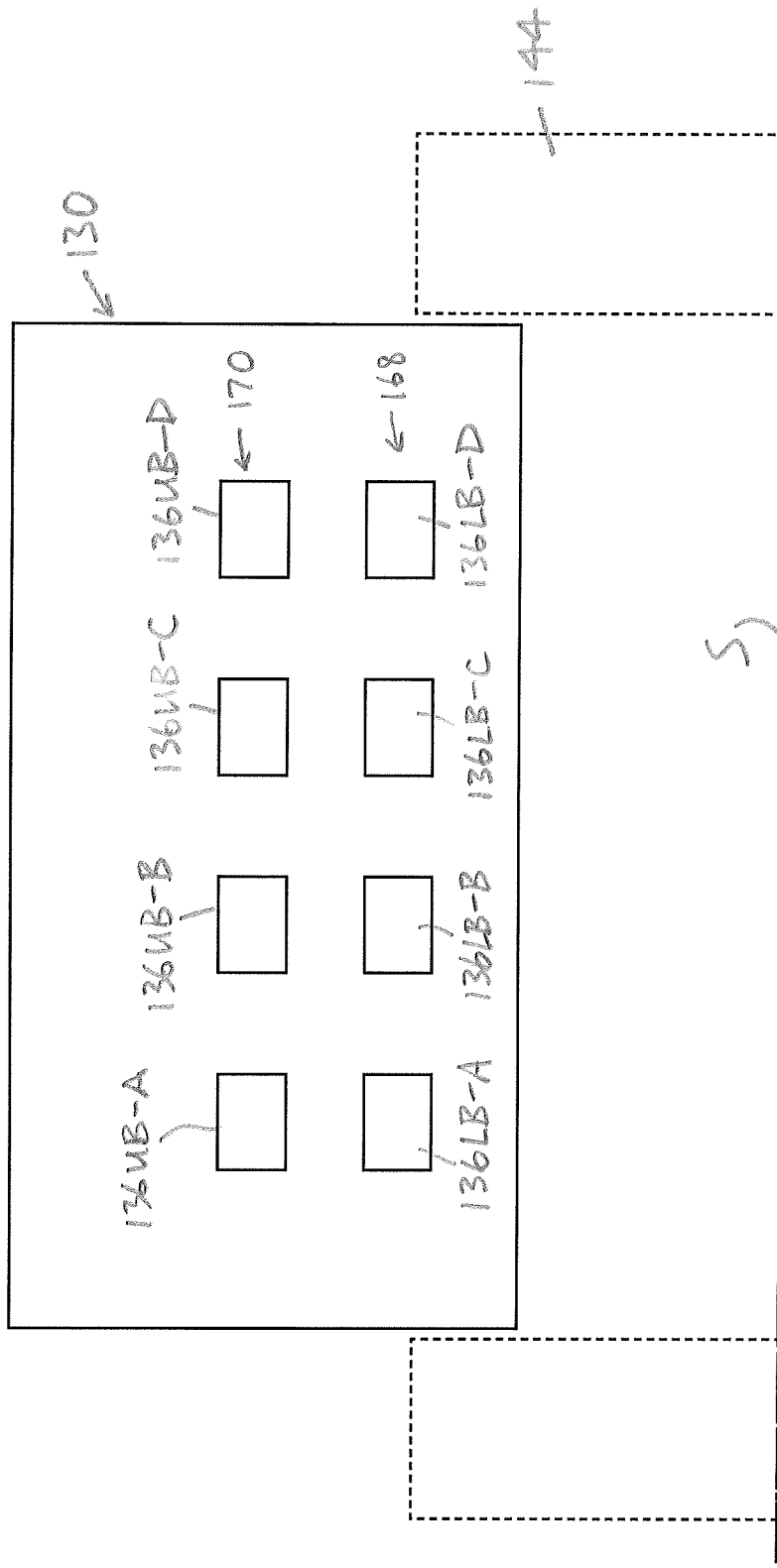
FIG. 9B is another schematic partial cross-section of the data-gathering unit of FIG. 8A, taken along line B-B in FIG. 8B.

FIGS. 9A and 9B are partial cross-sections of the data-gathering unit 130, taken along lines A-A and B-B respectively in FIG. 8B.

In one embodiment, the sensor assembly 134 preferably includes a number of front lower magnetic sensors (designated 136LF-A to 136LF-D in FIG. 9A for clarity of illustration) mounted to the frame assembly 132 in a first row 158 that is substantially orthogonal to the preselected direction of movement "$D_1$". Preferably, and as illustrated in FIG. 9B, the sensor assembly 134 also includes a number of front upper magnetic sensors (designated 136UF-A to 136UF-D for clarity of illustration) mounted to the frame assembly 132 in a second row 160 that is also substantially orthogonal to the preselected direction of movement "$D_1$" and substantially vertically aligned with the first row 158.

As illustrated in FIG. 9A, in one embodiment, it is preferred that there are four front lower magnetic sensors, identified individually as reference characters 136LF-A to 136LF-D for clarity of illustration. Similarly, the four front upper magnetic sensors are identified individually by reference characters 136UF-A to 136UF-D in FIG. 9B. However, it will be understood that any suitable number of magnetic sensors may be utilized.

As can be seen in FIGS. 8A and 8B, it is preferred that the frame assembly 132 extends between a front end 162 and an opposed back end 164 thereof, the front end 162 preceding the back end 164 when the data-gathering unit 130 is moving in the preselected direction "$D_1$". The first and second rows 158, 160 of the respective lower and upper magnetic sensors 136LF-A to 136LF-D, 136UF-A to 136UF-D are located between the front and back ends 162, 164, and at a first distance 166 from the front end 162 (FIG. 8B).

In an alternative embodiment, the sensor assembly 134 preferably includes a number of back lower magnetic sensors (designated 136LB-A to 136LB-D in FIG. 9B) located on the frame assembly in a third row 168 that is substantially orthogonal to the preselected direction of movement, and a number of back upper magnetic sensors (designated 136UB-A to 136UB-D in FIG. 9B) located in a fourth row 170 that is substantially orthogonal to the preselected direction of movement and substantially vertically aligned with the third row 168.

As can be seen in FIGS. 8B and 9B, in one embodiment, the third and fourth rows 168, 170 of the respective lower and upper magnetic sensors 136LB, 136UB are located between the front and back ends 162, 164, at a second distance 171 from the front end 162 that is greater than the first distance 166 (FIG. 8B).

The multiple magnetic sensors preferably are included in the data-gathering unit 130, and positioned in the lower and upper rows as described above, in order to provide multiple magnetic field data in respect of the same part of the rebar element 22. For instance, in FIG. 8B, an area of interest in or on the rebar element 22 is identified by the reference character "C".

In FIG. 8B, it can be seen that, subject to any acceleration to which the data-gathering unit 130 may be subjected, the front lower magnetic sensors 136LF-A to 136LF-D will pass over "C" at substantially the same time "t". Similarly, the front upper magnetic sensors 136UF-A to 136UF-D will also pass over "C" at the same time, "t". However, because each of the magnetic sensors in the first and second row 158, 160 is in a slightly different position relative to "C", each magnetic sensor provides slightly different magnetic field data about the area "C". Those skilled in the art would appreciate that the larger the number of the magnetic sensors sensing the magnetic flux density in the vicinity of "C", the better the composite magnetic field data based on such multiple magnetic sensors will be.

Similarly, the third and fourth rows 168, 170 of the magnetic sensors will pass over "C" at a different time, e.g., "t+1". The magnetic sensors in the third and fourth rows 168, 170 provide further additional magnetic field data about the magnetic field in the vicinity of "C", thereby facilitating improved magnetic field data about the area "C".

It is also preferred that the sensor assembly 134 includes a number of accelerometers 156. Each accelerometer preferably is located in a predetermined position relative to one or more of the magnetic sensors 136. In the arrangement illustrated in FIG. 8A, for example, one accelerometer 156 is positioned proximal to two magnetic sensors, designated 136LF-D and 136UF-D for convenience. Each accelerometer 156 is for sensing one or more acceleration of the magnetic sensor(s) to which it is proximally located. The acceleration causes one of the magnetic sensors to move relative to the concrete body at at least one modified velocity that differs from the preselected velocity. Each of the accelerometers is configured to transmit magnetic sensor acceleration data related to the acceleration to the processor 140. The processor 140 is configured for adjusting the anomaly data in view of the magnetic sensor acceleration data to provide magnetic sensor acceleration-adjusted anomaly data (FIG. 14). Accordingly, the magnetic field data and the location data provided in respect of the multiple magnetic sensors preferably is adjusted for such acceleration as may take place.

The rows 160 and 170 of the magnetic sensors 136 are also shown in FIG. 7. It will be understood that the magnetic sensors 136 in the rows 158 and 168 preferably are positioned substantially below the magnetic sensors 136 in the rows 160, 170 respectively. As can also be seen in FIG. 7, in one embodiment, the data-gathering unit 130 preferably includes a number of the accelerometers, positioned proximal to the magnetic sensors. For instance, as illustrated in FIG. 7, the data-gathering unit 130 preferably includes the accelerometers identified with reference characters 156A-156D respectively. It will be understood that the accelerometers 156A-156D are positioned proximal to the following magnetic sensors respectively:

136LF-A, 136UF-A, 136LB-A, and 136UB-A;
136LF-B, 136UF-B, 136LB-B, and 136UB-B;
136LF-C, 136UF-C, 136LB-C, and 136UB-C; and
136LF-D, 136UF-D, 136LB-D, and 136UB-D.

As described above, in addition to the stray magnetic field associated with the rebar element 22, and in addition to the background magnetic field, an ancillary or "artificial" magnetic field may also be considered. The ancillary or artificial magnetic field is associated with an external ferromagnetic body "E" (FIG. 8A) that is located in the vicinity of the reinforced structural element assembly 26. Those skilled in the art would appreciate that, because the magnetic field associated with the rebar element 22 in the reinforced structural element assembly 26 is sensed in situ, in practice, there may be other ferromagnetic bodies nearby. However, those skilled in the art would also appreciate that there may be circumstances in which there are no other such ferromagnetic bodies nearby.

Figure 15:
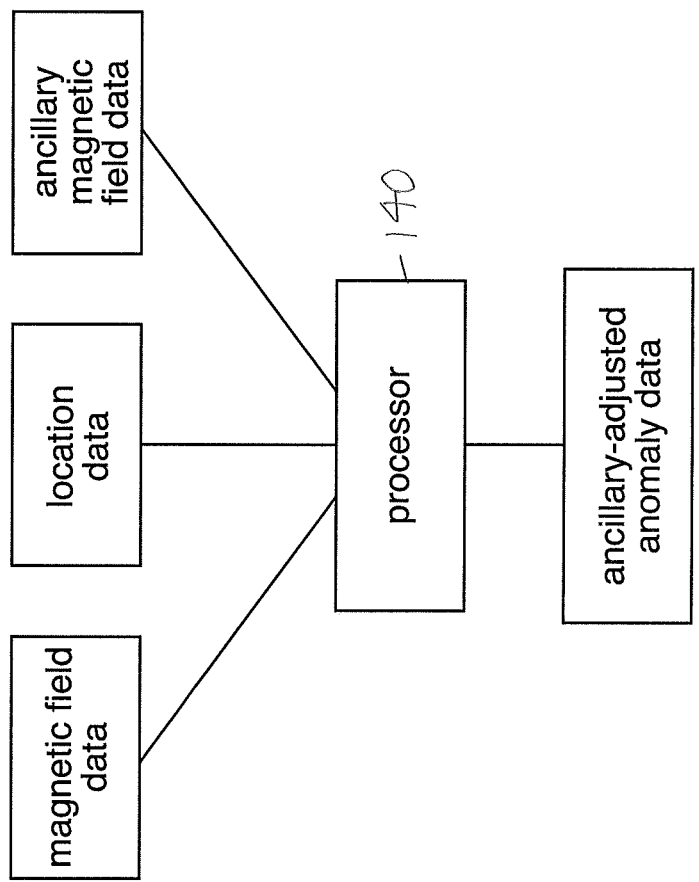
FIG. 15 is a block diagram illustrating another embodiment of the method of the invention.

In one embodiment, the sensor assembly 134 preferably includes one or more ancillary magnetic sensors 172 (FIG. 8A), for providing data about the ancillary magnetic field. The ancillary magnetic sensor 172 preferably senses at least part of an ancillary magnetic field associated with the external ferromagnetic body "E", to provide ancillary magnetic field data about the ancillary magnetic field. It is also preferred that the processor 140 is configured for adjusting the anomaly data in view of the ancillary magnetic field data to provide ancillary-adjusted anomaly data. The utilization of the magnetic field data, the location data, and the ancillary magnetic field data to provide the ancillary-adjusted anomaly data is schematically illustrated in FIG. 15.

Figure 10:
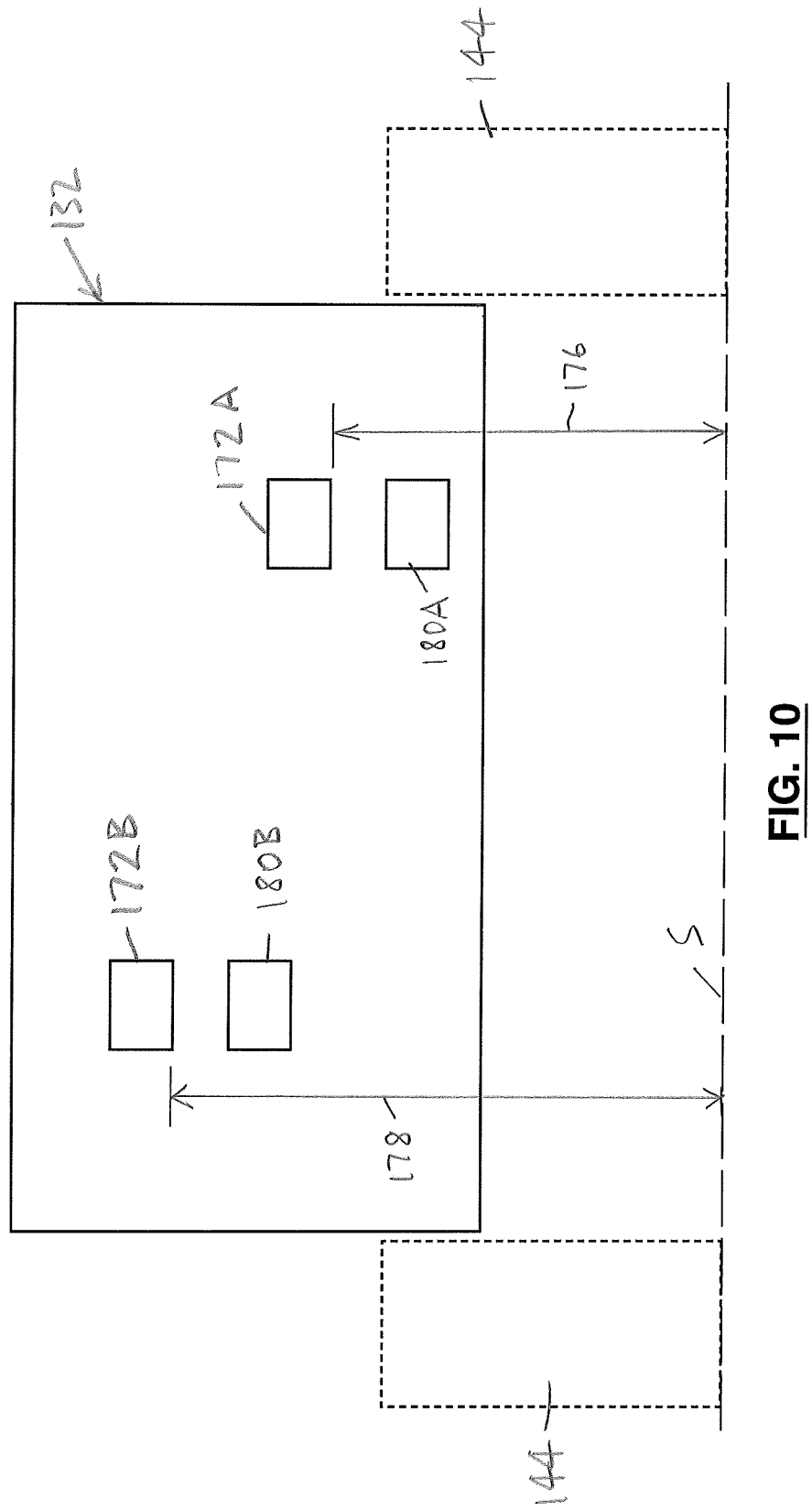
FIG. 10 is a schematic back view of the data-gathering unit of FIGS. 8A-9B.

For clarity of illustration, two ancillary magnetic sensors are illustrated in FIGS. 7 and 10, designated by reference characters 172A and 172B.

Figure 16:
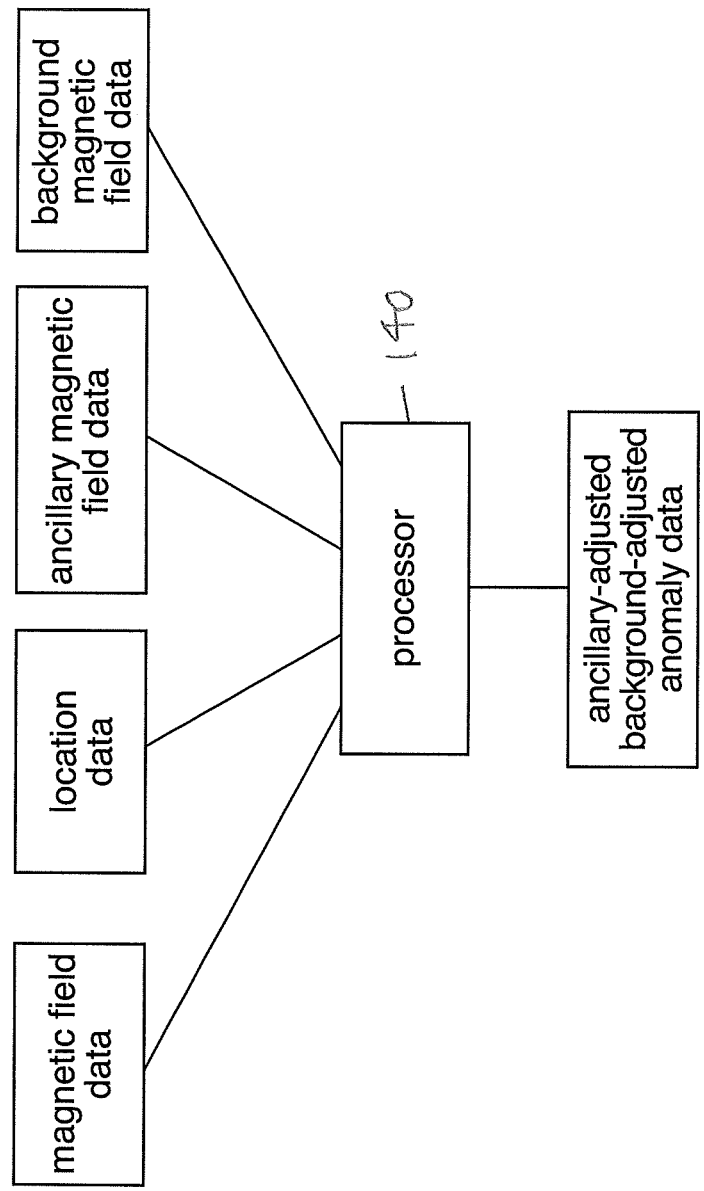
FIG. 16 is a block diagram illustrating another embodiment of the method of the invention.

Those skilled in the art would appreciate that the ancillary-adjusted anomaly data may be further adjusted by the processor to take the background magnetic field into account, resulting in ancillary-adjusted background-adjusted anomaly data. The utilization of the magnetic field data, the location data, the ancillary magnetic field data, and the background magnetic field data to provide ancillary-adjusted, background-adjusted anomaly data is schematically illustrated in FIG. 16.

As can be seen in FIGS. 8A and 8B, in one embodiment, the ancillary magnetic sensors 172A, 172B preferably are positioned in or on the data-gathering unit 130 apart from the magnetic sensors 136. It is also preferred that the ancillary magnetic sensors 172 are located between the front and back ends 162, 164 of the frame assembly 132, and are positioned at a preselected distance 174 from the back end 164 (FIG. 8B).

The sensor assembly 134 preferably includes the two ancillary magnetic sensors 172A and 172B. The ancillary magnetic sensors 172A, 172B preferably are positioned at the preselected distance 174 from the back end 164 and spaced apart laterally relative to the preselected direction.

It is also preferred that the ancillary magnetic sensors 172A, 172B are positioned at two different elevations 176, 178 respectively above the concrete body 24, when the data-gathering unit 130 is positioned on the preselected path. This can be seen, for example, in FIG. 10. The two ancillary magnetic sensors 172A, 172B preferably are positioned at two different elevations respectively in order to provide ancillary magnetic field data with enhanced accuracy. Because the ancillary magnetic sensors 172A, 172B are at two different elevations, the ancillary magnetic field data provided by them respectively is slightly different, and therefore may be combined to provide ancillary magnetic field data that is more accurate.

In one embodiment, the sensor assembly 134 preferably includes one or more ancillary accelerometers 180 located in a preselected ancillary location relative to the ancillary magnetic sensors 172A, 172B. Two ancillary accelerometers are identified by reference characters 180A, 180B in FIGS. 7 and 10, such ancillary accelerometers being positioned proximal to the ancillary magnetic sensors 172A, 172B to sense acceleration thereof. The ancillary accelerometer 180 preferably is positioned at a preselected ancillary accelerometer position relative to the ancillary magnetic sensors 172A, 172B. The ancillary accelerometers 180A, 180B preferably are configured for sensing one or more accelerations of the ancillary magnetic sensors 172A, 172B respectively. The acceleration causes one or both of the ancillary magnetic sensors to move relative to the concrete body 24 at at least one modified ancillary velocity that differs from the preselected velocity. The ancillary accelerometer 180 preferably is configured to transmit ancillary magnetic sensor acceleration data, related to the acceleration of the ancillary magnetic sensors 172A, 172B, to the processor 140. The processor 140 preferably is configured for adjusting the ancillary-adjusted anomaly data in view of the ancillary magnetic sensor acceleration data to provide ancillary magnetic sensor acceleration-adjusted ancillary-adjusted anomaly data.

Figure 17:
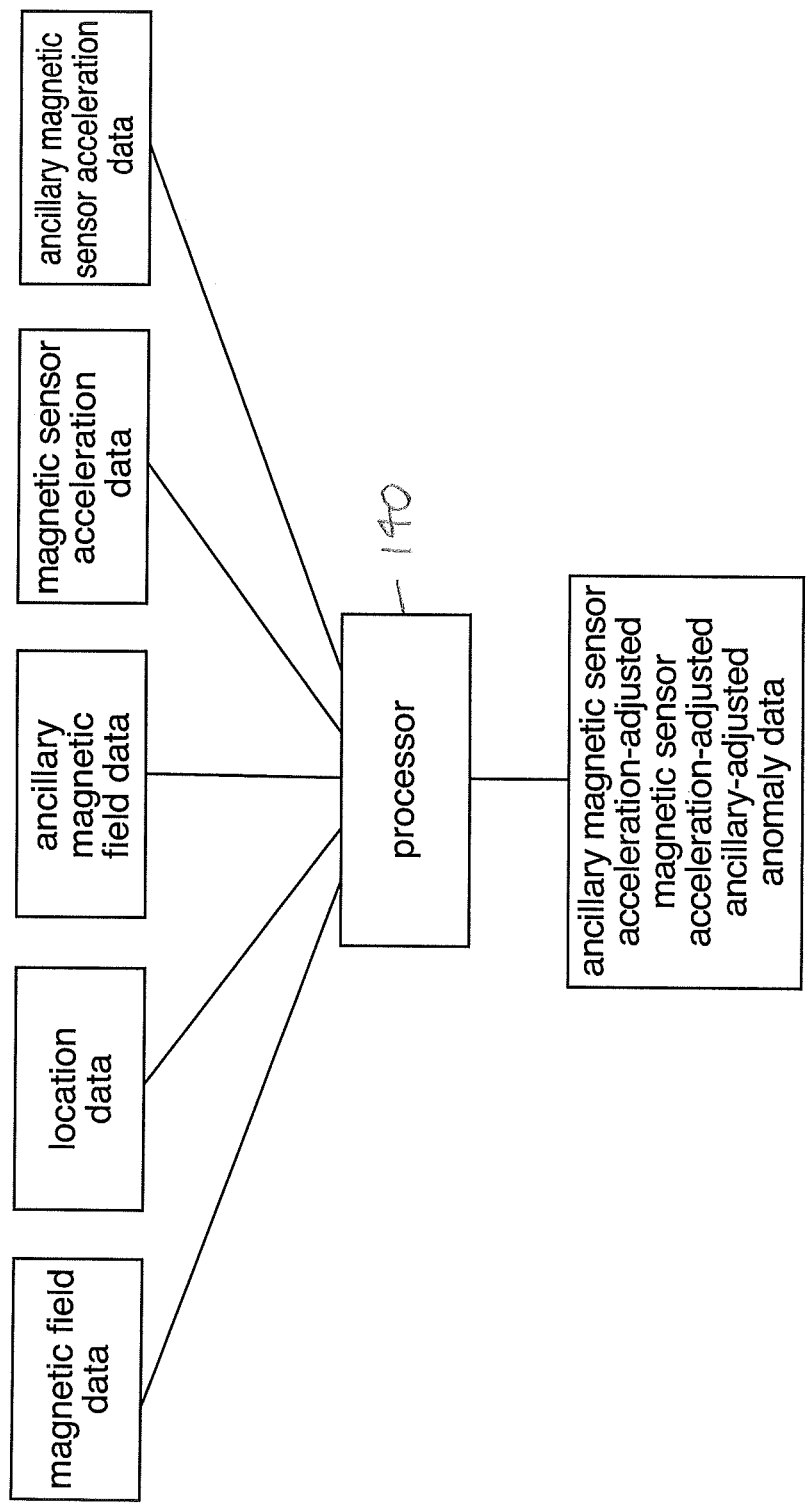
FIG. 17 is a block diagram illustrating another embodiment of the method of the invention.

The utilization of the magnetic field data, the location data, the ancillary magnetic field data, the magnetic sensor acceleration data, and the ancillary magnetic sensor acceleration data to provide the ancillary magnetic sensor acceleration-adjusted, magnetic sensor acceleration-adjusted, ancillary-adjusted anomaly data is schematically illustrated in FIG. 17.

Figure 18:
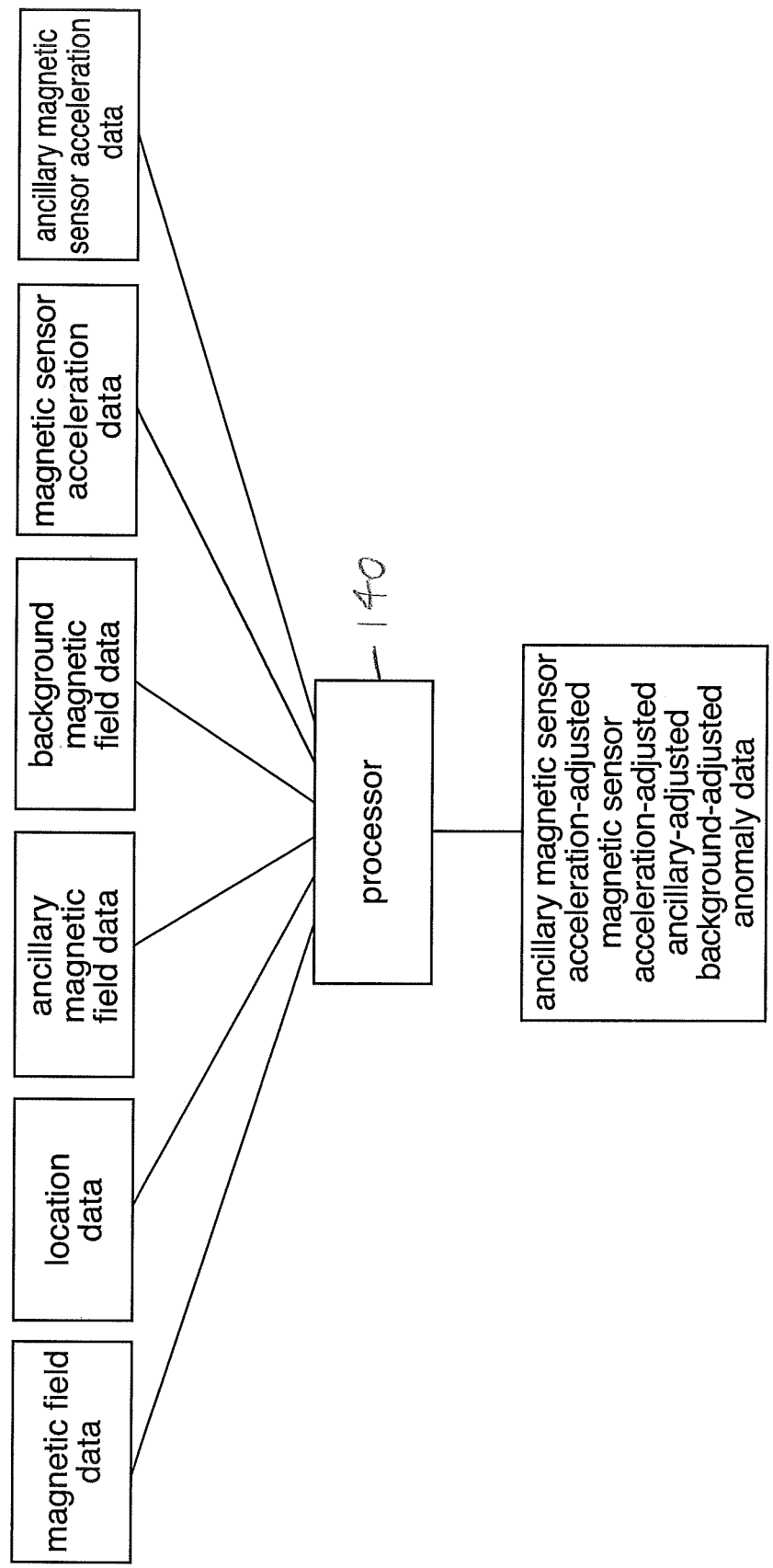
FIG. 18 is a block diagram illustrating another embodiment of the method of the invention.

As noted above, it is preferred that the background magnetic field be taken into account in determining whether an anomaly exists, and if so, the extent of the anomaly. The utilization of the magnetic field data, the location data, the ancillary magnetic field data, the ancillary magnetic sensor acceleration data, the magnetic sensor acceleration data, and the background magnetic field data to provide ancillary magnetic sensor acceleration-adjusted, magnetic sensor acceleration-adjusted, ancillary-adjusted, and background-adjusted anomaly data is schematically illustrated in FIG. 18.

It will be appreciated by those skilled in the art that the invention can take many forms, and that such forms are within the scope of the invention as claimed. The scope of the claims should not be limited by the preferred embodiments set forth in the examples, but should be given the broadest interpretation consistent with the description as a whole.

We claim:

1. A system for determining whether a stray magnetic field associated with an elongate rebar element at least partially positioned in a concrete body of a reinforced structural element assembly includes at least one anomaly, the system comprising:
   a data-gathering unit comprising:
      a frame assembly, movable relative to the reinforced structural element assembly in a preselected direction along a preselected path at a preselected velocity;
      a sensor assembly mounted to the frame assembly, the sensor assembly comprising at least one magnetic sensor for sensing at least part of the stray magnetic field as the sensor assembly is moved relative to the concrete body, to generate magnetic field data defining magnetic flux density of the stray magnetic field of the rebar element:
   at least one tracking assembly for generating location data to locate the magnetic field data relative to the concrete body;
   a processor for analyzing the magnetic field data for identifying said at least one anomaly, for analyzing the location data to locate said at least one anomaly relative to the concrete body, and for generating anomaly data describing said at least one anomaly;
   said at least one magnetic sensor being configured to sense at least part of the Earth's background magnetic field proximal to the reinforced structural element assembly, to generate background magnetic field data defining background magnetic flux density of the background magnetic field;
   the processor being configured for analyzing the background magnetic field data, to filter the magnetic field data with the background magnetic field data, to provide background-adjusted anomaly data;
   the sensor assembly additionally comprising:
      at least one ancillary magnetic sensor, for sensing at least part of an ancillary magnetic field in which the rebar element is located, to provide ancillary magnetic field data about the ancillary magnetic field;
      the processor being configured for adjusting the anomaly data in view of the ancillary magnetic field data to provide ancillary-adjusted anomaly data;
      at least one ancillary accelerometer located in a preselected ancillary location relative to said at least one ancillary magnetic sensor, said at least one ancillary accelerometer being positioned at a preselected ancillary accelerometer position relative to said at least one ancillary magnetic sensor; and
      said at least one ancillary accelerometer being configured for sensing at least one ancillary acceleration of said at least one ancillary magnetic sensor, said at least one ancillary acceleration causing said at least one ancillary magnetic sensor to move relative to the concrete body at at least one modified ancillary velocity that differs from the preselected velocity, wherein said at least one ancillary accelerometer is configured to transmit ancillary acceleration data related to said at least one ancillary acceleration to the processor, and wherein the processor is configured for adjusting the ancillary-adjusted anomaly data in view of the ancillary acceleration data to provide ancillary acceleration-adjusted ancillary-adjusted anomaly data.

* * * * *